United States Patent
Single et al.

(10) Patent No.: US 12,064,632 B2
(45) Date of Patent: Aug. 20, 2024

(54) METHOD AND DEVICE FOR FEEDBACK CONTROL OF NEURAL STIMULATION

(71) Applicant: Saluda Medical Pty Ltd, Artarmon (AU)

(72) Inventors: Peter Scott Vallack Single, Artarmon (AU); Dean Michael Karantonis, Artarmon (AU)

(73) Assignee: Saluda Medical Pty Ltd, Macquarie Park (AU)

(*) Notice: Subject to any disclaimer, the term of this patent is extended or adjusted under 35 U.S.C. 154(b) by 6 days.

(21) Appl. No.: 17/818,193

(22) Filed: Aug. 8, 2022

(65) Prior Publication Data

US 2023/0078685 A1 Mar. 16, 2023

Related U.S. Application Data

(63) Continuation of application No. 17/724,652, filed on Apr. 20, 2022, now Pat. No. 11,464,980, which is a
(Continued)

(30) Foreign Application Priority Data

Dec. 11, 2014 (AU) .................. 2014905031

(51) Int. Cl.
*A61N 1/36* (2006.01)
*A61N 1/05* (2006.01)

(52) U.S. Cl.
CPC ....... *A61N 1/36139* (2013.01); *A61N 1/0551* (2013.01); *A61N 1/36062* (2017.08); *A61N 1/36071* (2013.01)

(58) Field of Classification Search
CPC .............. A61N 1/36139; A61N 1/0551; A61N 1/36062; A61N 1/36071
See application file for complete search history.

(56) References Cited

U.S. PATENT DOCUMENTS

| | | |
|---|---|---|
| 3,724,467 A | 4/1973 | Avery et al. |
| 3,736,434 A | 5/1973 | Darrow |

(Continued)

FOREIGN PATENT DOCUMENTS

| | | |
|---|---|---|
| AU | 2013277009 | 1/2016 |
| CN | 103648583 | 3/2014 |

(Continued)

OTHER PUBLICATIONS

"Advanced Pain Therapy using Neurostimulation for Chronic Pain", Medtronic RestoreSensor clinical trial paper, Clinical summary, Nov. 2011, pp. 32.

(Continued)

*Primary Examiner* — Amanda K Hulbert
(74) *Attorney, Agent, or Firm* — Barnes & Thornburg LLP

(57) ABSTRACT

A method of controlling a neural stimulus by use of feedback. The neural stimulus is applied to a neural pathway in order to give rise to an evoked action potential on the neural pathway. The stimulus is defined by at least one stimulus parameter. A neural compound action potential response evoked by the stimulus is measured. From the measured evoked response a feedback variable is derived. A feedback loop is completed by using the feedback variable to control the at least one stimulus parameter value. The feedback loop adaptively compensates for changes in a gain of the feedback loop caused by electrode movement relative to the neural pathway.

29 Claims, 13 Drawing Sheets

Related U.S. Application Data continuation of application No. 17/532,725, filed on Nov. 22, 2021, now Pat. No. 11,344,729, which is a continuation of application No. 16/669,393, filed on Oct. 30, 2019, now Pat. No. 11,219,766, which is a continuation of application No. 15/535,008, filed as application No. PCT/AU2015/050787 on Dec. 11, 2015, now Pat. No. 10,500,399.

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | van den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van Oort et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,332,047 B2 | 12/2012 | Libbus et al. |
| 8,359,102 B2 | 1/2013 | Thacker et al. |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,538,541 B2 | 9/2013 | Milojevic et al. |
| 8,588,929 B2 | 11/2013 | Davis et al. |
| 8,620,459 B2 | 12/2013 | Gibson et al. |
| 8,655,002 B2 | 2/2014 | Parker |
| 8,670,830 B2 | 3/2014 | Carlson et al. |
| 8,886,323 B2 | 11/2014 | Wu et al. |
| 8,945,216 B2 | 2/2015 | Parker et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,566,439 B2 | 2/2017 | Single et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 11,219,766 B2 | 1/2022 | Single et al. |
| 11,344,729 B1 | 5/2022 | Single et al. |
| 11,464,980 B2 | 10/2022 | Single et al. |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |

(56) References Cited

U.S. PATENT DOCUMENTS

| | | |
|---|---|---|
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0276722 A1 | 12/2006 | Litvak et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0030337 A1 | 1/2009 | Gozani et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey et al. |
| 2009/0157155 A1 | 6/2009 | Bradley et al. |
| 2009/0270957 A1 | 10/2009 | Pianca |
| 2009/0281594 A1 | 11/2009 | King et al. |
| 2009/0287277 A1 | 11/2009 | Conn et al. |
| 2009/0299214 A1 | 12/2009 | Wu et al. |
| 2009/0306491 A1 | 12/2009 | Haggers |
| 2009/0306533 A1 | 12/2009 | Rousche et al. |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0268043 A1 | 10/2013 | Tasche et al. |
| 2013/0289661 A1 | 10/2013 | Griffith et al. |
| 2013/0289683 A1 | 10/2013 | Parker et al. |
| 2014/0046407 A1 | 2/2014 | Ben-Ezra et al. |
| 2014/0066803 A1 | 5/2014 | Takahashi et al. |
| 2014/0142447 A1 | 7/2014 | Parker et al. |
| 2014/0194771 A1 | 7/2014 | Single et al. |
| 2014/0194772 A1 | 8/2014 | Parker et al. |
| 2014/0236042 A1 | 8/2014 | Parker et al. |
| 2014/0236257 A1 | 8/2014 | Parker |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0051637 A1 | 2/2015 | Osorio |
| 2015/0126839 A1 | 5/2015 | Li et al. |
| 2015/0148869 A1 | 5/2015 | Dorvall et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |
| 2016/0082268 A1 | 3/2016 | Hershey et al. |
| 2016/0101289 A1 | 4/2016 | Stolen et al. |
| 2016/0106980 A1 | 4/2016 | Surth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |

(56) References Cited

U.S. PATENT DOCUMENTS

| | | |
|---|---|---|
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0157410 A1 | 6/2017 | Moffitt et al. |
| 2017/0173326 A1 | 6/2017 | Bloch et al. |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0001139 A1 | 1/2019 | Mishra et al. |
| 2019/0030339 A1 | 1/2019 | Baru et al. |
| 2019/0125269 A1 | 5/2019 | Markovic et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |

FOREIGN PATENT DOCUMENTS

| | | |
|---|---|---|
| CN | 103654762 | 3/2014 |
| CN | 103842022 | 6/2014 |
| CN | 104411360 | 3/2015 |
| EP | 219084 | 4/1987 |
| EP | 1244496 | 10/2002 |
| EP | 998958 | 8/2005 |
| EP | 2019716 | 11/2007 |
| EP | 2243510 | 10/2010 |
| EP | 2443995 | 4/2012 |
| EP | 2520327 | 11/2012 |
| EP | 2707095 | 3/2014 |
| EP | 3229893 | 10/2017 |
| JP | 2006504494 | 2/2006 |
| JP | 2009512505 | 3/2009 |
| JP | 2012524629 | 10/2012 |
| JP | 2013500779 | 1/2013 |
| JP | 2013527784 | 7/2013 |
| JP | 2013536044 | 9/2013 |
| JP | 2014522261 | 9/2014 |
| JP | 2014523261 | 9/2014 |
| WO | WO 1983003191 | 9/1983 |
| WO | WO 1993001863 | 2/1993 |
| WO | WO 1996012383 | 4/1996 |
| WO | WO 2000002623 | 1/2000 |
| WO | WO 2002036003 | 11/2001 |
| WO | WO 2002038031 | 5/2002 |
| WO | WO 2002049500 | 6/2002 |
| WO | WO 2002082982 | 10/2002 |
| WO | WO 2003028521 | 4/2003 |
| WO | WO 2003043690 | 5/2003 |
| WO | WO 2003103484 | 12/2003 |
| WO | WO 2004021885 | 3/2004 |
| WO | WO 2004103455 | 12/2004 |
| WO | WO 2005032656 | 4/2005 |
| WO | WO 2005105202 | 11/2005 |
| WO | WO 2005122887 | 12/2005 |
| WO | WO 2006091636 | 8/2006 |
| WO | WO 2007050657 | 5/2007 |
| WO | WO 2007064936 | 6/2007 |
| WO | WO 2007127926 | 11/2007 |
| WO | WO 2007130170 | 11/2007 |
| WO | WO 2008004204 | 1/2008 |
| WO | WO 2008049199 | 5/2008 |
| WO | WO 2009002072 | 12/2008 |
| WO | WO 2009002579 | 12/2008 |
| WO | WO 2009010870 | 1/2009 |
| WO | WO 2009130515 | 10/2009 |
| WO | WO 2009146427 | 12/2009 |
| WO | WO 2010013170 | 2/2010 |
| WO | WO 2010044989 | 4/2010 |
| WO | WO 2010051392 | 5/2010 |
| WO | WO 2010051406 | 5/2010 |
| WO | WO 2010057046 | 5/2010 |
| WO | WO 2010124139 | 10/2010 |
| WO | WO 2010138915 | 12/2010 |
| WO | WO 2011011327 | 1/2011 |
| WO | WO 2011014570 | 2/2011 |
| WO | WO 2011017778 | 2/2011 |
| WO | WO 2011066477 | 6/2011 |
| WO | WO 2011066478 | 6/2011 |
| WO | WO 2011112843 | 9/2011 |
| WO | WO 2011119251 | 9/2011 |
| WO | WO 2011159545 | 12/2011 |
| WO | WO 2012027252 | 3/2012 |
| WO | WO 2012027791 | 3/2012 |
| WO | WO 2012155183 | 11/2012 |
| WO | WO 2012155184 | 11/2012 |
| WO | WO 2012155185 | 11/2012 |
| WO | WO 2012155187 | 11/2012 |
| WO | WO 2012155188 | 11/2012 |
| WO | WO 2012155189 | 11/2012 |
| WO | WO 2012155190 | 11/2012 |
| WO | WO 2012162349 | 11/2012 |
| WO | WO 2013063111 | 5/2013 |
| WO | WO 2013075171 | 5/2013 |
| WO | WO 2014071445 | 5/2014 |
| WO | WO 2014071446 | 5/2014 |
| WO | WO 2014143577 | 9/2014 |
| WO | WO 2014150001 | 9/2014 |
| WO | WO 2015070281 | 5/2015 |
| WO | WO 2015074121 | 5/2015 |
| WO | WO 2015109239 | 7/2015 |
| WO | WO 2015143509 | 10/2015 |
| WO | WO 2015168735 | 11/2015 |
| WO | WO 2016011512 | 1/2016 |
| WO | WO 2016048974 | 3/2016 |
| WO | WO 2016059556 | 4/2016 |
| WO | WO 2016077882 | 5/2016 |
| WO | WO 2016090420 | 6/2016 |
| WO | WO 2016090436 | 6/2016 |
| WO | WO 2016115596 | 7/2016 |
| WO | WO 2016161484 | 10/2016 |
| WO | WO 2016168798 | 10/2016 |
| WO | WO 2016191807 | 12/2016 |
| WO | WO 2016191808 | 12/2016 |
| WO | WO 2016191815 | 12/2016 |
| WO | WO 2017053504 | 3/2017 |
| WO | WO 2017142948 | 8/2017 |
| WO | WO 2017173493 | 10/2017 |
| WO | WO 2017210352 | 12/2017 |
| WO | WO 2017219096 | 12/2017 |
| WO | WO 2018080753 | 5/2018 |
| WO | WO 2018119220 | 6/2018 |
| WO | WO 2018160992 | 9/2018 |
| WO | WO 2018170141 | 9/2018 |
| WO | WO 2019178634 | 9/2019 |
| WO | WO 2019204884 | 10/2019 |
| WO | WO 2019231796 | 12/2019 |
| WO | WO 2020082118 | 4/2020 |
| WO | WO 2020082126 | 4/2020 |
| WO | WO 2020082128 | 4/2020 |
| WO | WO 2020087123 | 5/2020 |

(56) References Cited

FOREIGN PATENT DOCUMENTS

| WO | WO 2020087135 | 5/2020 |
|----|---------------|--------|
| WO | WO 2020124135 | 6/2020 |

OTHER PUBLICATIONS

"Battelle Neurotechnology—Moving Beyond The Limits In Neurotechnology", Battelle, www.battelle.org, May 2014, pp. 1-2.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-Mar. 2000, Oct. 15, 2000.
"Neural Bypass Technology Enables Movement in Paralyzed Patient", Posted on Jul. 29, 2014, 6 a.m. in Brain chips/computer interface, pp. 1-2.
"Percutaneous Lead Kit," St. Jude Medical Clinician's Manual, Models 3143, 3146, 3149, 3153, 3156, 3159, 3183, 3186, 3189, published Sep. 2016, 24 pages.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Abrard et al., "A time-frequency blindsignal separation methodapplicable to underdetermined mixtures of dependent sources," Signal Processing 85 (2005), pp. 1389-1403.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen, S. et al. "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Australian Examination Report for Application No. 2019283936, Mailed Apr. 1, 2021, 7 pages.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Balzer et al., "Localization of cervical and cervicomedullary stimulation leads for pain treatment using median nerve somatosensay evoked potential collision testing", Journal of Neurosurgery, Jan. 2011, vol. 114, No. 1, pp. 200-205.
Baratta et al., "Orderly Stimulation of Skeletal Muscle Motor Units with Tripolar Nerve Cuff Electrode," IEEE Transactions on Biomedical Engineering, vol. 36, No. 8, 1989, pp. 836-842.
Blum, A. R. "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992. pp. 2600-2601.
Casey et al., "Separation of Mixed Audio Sources by Independent Subspace Analysis," Mitsubishi Electric Research Laboratories (2001), 8 pgs.
Celestin et al., "Pretreatment Psychosocial Variables as Predictors of Outcomes Following Lumbar Surgery and Spinal Cord Stimulation: A Systematic Review and Literature Synthesis," American Academy of Pain Medicine, 2009, vol. 10, No. 4, pp. 639-653, doi: 10.1111/j.1526-4637.2009.00632.X.
Cong et al., "A 32-channel modular bi-directional neural interface system with embedded DSP for closed-loop operation," 40th European Solid State Circuits Conference (ESSCIRC), 2014, pp. 99-102.
Connolly et al., "Towards a platform for prototyping control systems for optimization of neuromodulation therapies," IEEE Biomedical Circuits and Systems Conference (BioCAS), 2015, pp. 1-4.
Coquery et al., "Backward and forward masking in the perception of cutaneous stimuli", Perception & Psychophysics, 1973, vol. 13.No. 2, pp. 161-163.
Dawson, G.D. "The relative excitability and conduction velocity of sensory and motor nerve fibres in man", Journal of Physiology, 1956, vol. 131 (2), pp. 436-451.
De Ridder et al., "Burst Spinal Cord Stimulation toward Paresthesia-Free Pain Suppression", Nuerosurgery-online.com, May 2010, vol. 66, No. 8, pp. 986-990.
Delgado et al., "Measurement and interpretation of electrokinetic phenomena," Pure Appl. Chem., 2005, vol. 77, No. 10, pp. 1753-1805.
Devergnas et al., A "Cortical potentials evoked by deep brain stimulation in the subthalamic area", Front Syst Neurosci. 2011; 5: 30. May 13, 2011. doi: 10.3389/fnsys.2011.00030.
Dijkstra, E. A. "Ultrasonic Distance Detection for a Closed-Loop Spinal Cord Stimulation System", Proceedings—19th International Conference—IEEE/EMBS Oct. 30-Nov. 2, 1997, Chicago, IL., 4 pgs.
Dillier, N et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi: 10.1152/jn.00729.2002.
England et al., "Increased Numbers of Sodium Channels Form Along Demyelinated Axons", Brain Research 548, No. 1-2 (May 10, 1991): 334-337.
European Search Report for European Application 12785619.3 Search Completed Oct. 13, 2014, Mailed Oct. 23, 2014, 7 pgs.
European Search Report for European Application 12785669.8 Search Completed Sep. 22, 2014, Mailed Sep. 29, 2014, 5 pgs.
European Search Report for European Application No. 15861444.6, Search completed Jul. 13, 2018, Mailed Jul. 23, 2018, 8 pgs.
Extended European Search Report for EP Application 12785483.4 completed Sep. 16, 2014, 7 pgs.
Extended European Search Report for European Application No. 11820923.8, report completed Dec. 9, 2013, report mailed Dec. 17, 2013, 6 pgs.
Extended European Search Report for European Application No. 13852669.4, Search completed Jun. 8, 2016, Mailed Jun. 22, 2016, 09 pgs.
Extended European Search Report for European Application No. 14861553.7, Search completed Jun. 8, 2017, Mailed Jun. 19, 2017, 8 pgs.
Extended European Search Report for European Application No. 14863597.2, Search completed Jun. 6, 2017, Mailed Jun. 13, 2017, 9 pgs.
Extended European Search Report for European Application No. 15768956.3, Search completed Oct. 3, 2017, Mailed Oct. 10, 2017, 8 pgs.
Extended European Search Report for European Application No. 15789515.2, Search completed Dec. 4, 2017, Mailed Jan. 30, 2018, 7 pgs.

(56) References Cited

OTHER PUBLICATIONS

Extended European Search Report for European Application No. 16739680.3, Search completed Jun. 1, 2018, Mailed Jun. 12, 2018, 9 pgs.
Extended European Search Report for European Application No. 16802237.4, Search completed Dec. 11, 2018, Mailed Dec. 19, 2018, 9 pgs.
Extended European Search Report for European Application No. 16802238.2, Search completed Oct. 17, 2018, Mailed Oct. 24, 2018, 8 pgs.
Extended European Search Report for European Application No. 17778477.4, report completed Nov. 12, 2019, mailed Nov. 20, 2019, 7 pgs.
Extended European Search Report for European Application No. 17814341.8, report completed Dec. 12, 2019, report mailed Jan. 2, 2020, 8 pgs.
Extended European Search Report for European Application No. 13853514.1, Search completed Jun. 8, 2016, Mailed Jun. 15, 2016, 07 pgs.
Extended European Search Report in European Appln No. 18910394. 8, dated Oct. 15, 2021, 8 pages.
Extended European Search Report in European Appln No. 19793420. 1, dated Dec. 17, 2021, 9 pages.
Extended European Search Report in European Appln No. 19875139. 8, dated Jun. 15, 2022, 8 pages.
Extended European Search Report in European Appln No. 19899138. 2, dated Aug. 3, 2022, 9 pages.
Fagius, J. et al. "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Fisher, "F-Waves—Physiology and Clinical Uses", TheScientific WorldJournal, (2007) 7, pp. 144-160.
Fitzpatrick et al., "A Nerve Cuff Design for the Selective Activation and Blocking of Myelinated Nerve Fibers," IEEE Engineering in Medicine and Biology Society, vol. 13, No. 2, 1991, pp. 906-907.
Franke et al., Felix "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
George et al., "Vagus nerve stimulation: a new tool for brain research and therapy", Biological Psychiatry 47, No. 4, Feb. 15, 2000, pp. 287-295.
Gmel et al., "A new biomarker for closed-loop deep brain stimulation in the subthalamic nucleus for patients with Parkinson's disease," IEEE 2014 Biomedical Circuits and Systems Conference, BioCAS 2014—Proceedings. 500-503. (abstract only).
Gnadt et al., "Spectral Cancellation of Microstimulation Artifact for Simultaneous Neural Recording in Situ", IEEE Transactions on Biomedical Engineering, Oct. 2003, Date of Publication: Sep. 23, 2003, vol. 50, No. 10, pp. 1129-1135, DOI: 10.1109/TBME.2003. 816077.
Goodall, E. V. "Modeling Study of Activation and Propagation delays During Stimulation of Peripheral Nerve Fibres with a Tri polar Cuff Electrode", IEEE Transactions on Rehabilitation Engineering, vol. 3, No. 3, Sep. 1995, pp. 272-282.
Gorman et al., "ECAP Mapping of the Spinal Cord: Influence of Electrode Position on Aβ Recruitment", (2012)., in 16th Annual Meeting. Presented at the North American Neuromodulation Society, Las Vegas, NV.
Gorman et al., "Neural Recordings For Feedback Control of Spinal Cord Stimulation: Reduction of Paresthesia Variability.", 2013, in International Neuromodulation Society 11th World Congress. Presented at the International Neuromodulation Society 11th World Congress, Berlin, Germany.
Hallstrom et al, "Distribution of lumbar spinal evoked potentials and their correlation with stimulation-induced paresthesiae", (1991), Electroencephalography and clinical neurophysiology 80: 126-139.
Harper, A. A. et al., "Conduction Velocity is Related to Morphological Cell Type in Rat Dorsal Root Ganglion Neurones", J. Physiol, (1985), 359, pp. 31-46.
He et al., "Perception threshold and electrode position for spinal cord stimulation", Pain, 59 (1994) 55-63 pages.
Herreras, "Local Field Potentials: Myths and Misunderstandings", Frontiers in Neural Circuits, Dec. 15, 2016, vol. 10, Article 1101, 16 pgs.
Holsheimer et al., "Optimum Electrode Geometry for Spinal Cord Stimulation: the Narrow Bipole and Tripole", Medical and Biological Engineering and Computing, 35, No. 5, 1997, pp. 493-497.
Holsheimer et al., "Significance of the Spinal Cord Position in Spinal Cord Stimulation", Acta Neurochir (1995) [Suppl] 64: 119-124 pages.
Holsheimer et al., "Spinal Geometry and Paresthesia Coverage in Spinal Cord Stimulation", Neuromodulation, 1998, vol. 1, No. 3, pp. 129-136.
Howell et al., "Evaluation of Intradural Stimulation Efficiency and Selectivity in a Computational Model of Spinal Cord Stimulation," PLoS One, DOI:10.1371/journal.pone.0114938, Dec. 23, 2014, 25 pages.
Huff, Terry B. et al., "Real-Time CARS Imaging Reveals a Calpain-Dependent Pathway for Paranodal Myelin Retraction during High-Frequency Stimulation", PLoS One vol. 6, issue 3 (Mar. 3, 2011): e17176, 11 pgs.
International Preliminary Report for International Application No. PCT/AU2017/050296, Issued Oct. 9, 2018, 7 pgs.
International Preliminary Report for International Application No. PCT/AU2017/050647, Issued Dec. 25, 2018, 8 pgs.
International Preliminary Report for International Application No. PCT/AU2019/050384, Mailed Oct. 27, 2020, 8 pgs.
International Preliminary Report on Patentability for International Application No. PCT/AU2011/001127, Report Issued Mar. 5, 2013, 9 pgs.
International Preliminary Report on Patentability for International Application No. PCT/AU2012/000511, Report Issued Nov. 19, 2013, 6 pgs.
International Preliminary Report on Patentability for International Application No. PCT/AU2012/000512, Report Issued Nov. 19, 2013, 8 pgs.
International Preliminary Report on Patentability for International Application No. PCT/AU2012/000513, Report Issued Nov. 19, 2013, 11 pgs.
International Preliminary Report on Patentability for International Application No. PCT/AU2012/000515, Report Issued Nov. 19, 2013, 5 pgs.
International Preliminary Report on Patentability for International Application No. PCT/AU2012/000516, Report Issued Nov. 19, 2013, 9 pgs.
International Preliminary Report on Patentability for International Application No. PCT/AU2012/000517, Report Issued Nov. 19, 2013, 6 pgs.
International Preliminary Report on Patentability for International Application No. PCT/AU2012/000518, Report Issued Nov. 19, 2013, 11 pgs.
International Preliminary Report on Patentability for International Application No. PCT/AU2012/001441, Report Issued May 27, 2014, 10 pgs.
International Preliminary Report on Patentability for International Application No. PCT/AU2013/001279, Report Issued May 12, 2015, 6 pgs.

(56) References Cited

OTHER PUBLICATIONS

International Preliminary Report on Patentability for International Application No. PCT/AU2013/001280, Report Issued May 12, 2015, 6 pgs.
International Preliminary Report on Patentability for International Application No. PCT/AU2014/001049, Report Issued May 17, 2016, 5 pgs.
International Preliminary Report on Patentability for International Application No. PCT/AU2014/050369, Report Issued May 24, 2016, 8 pgs.
International Preliminary Report on Patentability for International Application No. PCT/AU2015/050135, Report Issued Oct. 4, 2016, 13 pgs.
International Preliminary Report on Patentability for International Application No. PCT/AU2015/050215, Report Issued Nov. 8, 2016, 4 pgs.
International Preliminary Report on Patentability for International Application No. PCT/AU2015/050422, Report Issued Jan. 31, 2017, 8 pgs.
International Preliminary Report on Patentability for International Application No. PCT/AU2015/050724, Report Issued May 23, 2017, 5 pgs.
International Preliminary Report on Patentability for International Application No. PCT/AU2015/050753, Report Issued Jun. 13, 2017, 7 pgs.
International Preliminary Report on Patentability for International Application No. PCT/AU2015/050787, Report Issued Jun. 13, 2017, 6 pgs.
International Preliminary Report on Patentability for International Application No. PCT/AU2016/050019, Report Issued Jul. 25, 2017, 9 pgs.
International Preliminary Report on Patentability for International Application No. PCT/AU2016/050263, Report Issued Oct. 10, 2017, 9 pgs.
International Preliminary Report on Patentability for International Application No. PCT/AU2018/050278, Issued Sep. 29, 2020, 7 pgs.
International Search Report & Written Opinion for International Application No. PCT/AU2013/001280, Search Completed Jan. 16, 2014, Mailed Jan. 16, 2014, 8 pgs.
International Search Report & Written Opinion for International Application PCT/AU2013/001279, Search Completed Jan. 9, 2014, Mailed Jan. 9, 2014, 9 Pgs.
International Search Report and Written Opinion for International Application No. PCT/AU2011/001127, date completed Nov. 11, 2011, date mailed Nov. 15, 2011, 13 pgs.
International Search Report and Written Opinion for International Application No. PCT/AU2012/001441, International Filing Date Nov. 23, 2012, Search Completed Feb. 26, 2013, Mailed Feb. 26, 2013, 14 pgs.
International Search Report and Written Opinion for International Application No. PCT/AU2014/001049, Search completed Feb. 10, 2015, Mailed Feb. 10, 2015, 8 pgs ..
International Search Report and Written Opinion for International Application No. PCT/AU2014/050369, Search completed Feb. 20, 2015, Mailed Feb. 20, 2015, 14 pgs.
International Search Report and Written Opinion for International Application No. PCT/AU2015/050135, Search completed Jun. 30, 2015, Mailed Jun. 30, 2015, 26 pgs.
International Search Report and Written Opinion for International Application No. PCT/AU2015/050215, Search completed Jul. 30, 2015, Mailed Jul. 30, 2015, 8 pgs.
International Search Report and Written Opinion for International Application No. PCT/AU2015/050422, Search completed Oct. 14, 2015, Mailed Oct. 14, 2015, 17 pgs.
International Search Report and Written Opinion for International Application No. PCT/AU2015/050724, Search completed May 9, 2016, Mailed May 9, 2016, 8 pgs.
International Search Report and Written Opinion for International Application No. PCT/AU2015/050753, Search completed Feb. 10, 2016, Mailed Feb. 10, 2016, 10 pgs.

International Search Report and Written Opinion for International Application No. PCT/AU2015/050787, Search completed Mar. 16, 2016, Mailed Mar. 16, 2016, 10 pgs.
International Search Report and Written Opinion for International Application No. PCT/AU2016/050019, Search completed May 4, 2016, Mailed May 4, 2016, 16 pgs.
International Search Report and Written Opinion for International Application No. PCT/AU2016/050263, Search completed Nov. 16, 2016, Mailed Nov. 16, 2016, 8 pgs.
International Search Report and Written Opinion for International Application No. PCT/AU2016/050430, Search completed Aug. 16, 2016, Mailed Aug. 16, 2016, 10 pgs.
International Search Report and Written Opinion for International Application No. PCT/AU2016/050431, Search completed Aug. 16, 2016, Mailed Aug. 16, 2016, 11 pgs.
International Search Report and Written Opinion for International Application No. PCT/AU2016/050439, Search completed Jul. 15, 2016, Mailed Jul. 15, 2016, 8 pgs.
International Search Report and Written Opinion for International Application No. PCT/AU2017/050296, Search completed Jul. 28, 2017, Mailed Jul. 28, 2017, 10pgs.
International Search Report and Written Opinion for International Application No. PCT/AU2017/050647, Search completed Sep. 29, 2017, Mailed Sep. 29, 2017, 13 pgs.
International Search Report and Written Opinion for International Application No. PCT/AU2018/050278, Search completed Jun. 18, 2018, Mailed Jun. 18, 2018, 12 pgs.
International Search Report and Written Opinion for International Application No. PCT/AU2019/050384, Search completed Jun. 25, 2019, Mailed Jun. 25, 2019, 15 pgs.
International Search Report and Written Opinion for International Application No. PCT/AU2019/051385, Search completed Mar. 24, 2020, Mailed Mar. 24, 2020, 8 Pgs.
International Search Report for Australian Application 2011901829, Search Completed Feb. 6, 2012, Mailed Feb. 7, 2012, 3 pgs.
International Search Report for International Application No. PCT/AU2012/000512, International Filing Date May 11, 2012, Search Completed Jul. 10, 2012, Mailed Jul. 11, 2012, 4 pgs.
International Search Report for International Application No. PCT/AU2019/051151, International Filing Date Oct. 22, 2019, Search Completed Feb. 24, 2020, Mailed Feb. 24, 2020, 9 pgs.
International Search Report for International Application No. PCT/AU2019/051160, International Filing Date Oct. 23, 2019, Search Completed Jan. 28, 2020, Mailed Jan. 28, 2020, 13 pgs.
International Search Report for International Application No. PCT/AU2019/051163, International Filing Date Oct. 23, 2019, Search Completed Jan. 21, 2020, Mailed Jan. 31, 2020, 8 pgs.
International Search Report for International Application No. PCT/AU2012/000511, International Filing Date May 11, 2012, Search Completed May 17, 2012, Mailed May 18, 2012, 4 pgs.
International Search Report for International Application No. PCT/AU2012/000513, International Filing Date May 11, 2012, Search Completed May 29, 2012, Mailed May 30, 2012, 5 pgs.
International Search Report for International Application No. PCT/AU2012/000515, International Filing Date May 11, 2012, Search Completed May 21, 2012, Mailed Jun. 4, 2012, 5 pgs.
International Search Report for International Application No. PCT/AU2012/000516, International Filing Date May 11, 2012, Search Completed Jul. 11, 2012, Mailed Jul. 12, 2012, 8 pgs.
International Search Report for International Application No. PCT/AU2012/000517, International Filing Date May 11, 2012, Search Completed Jun. 4, 2012, Mailed Jun. 6, 2012, 3 pgs.
International Search Report for International Application No. PCT/AU2012/000518, International Filing Date May 11, 2012, Search Completed Jun. 8, 2012, Mailed Jun. 12, 2012, 4 pgs.
International Search Report for International Application No. PCT/AU2019/051197, International Filing Date Oct. 30, 2019, Search Completed Jan. 21, 2020, Mailed Jan. 21, 2020, 15 pgs.
International Search Report for International Application No. PCT/AU2019/051210, International Filing Date Nov. 2, 2019, Search Completed Feb. 4, 2020, Mailed Feb. 4, 2020, 10 pgs.

(56) References Cited

OTHER PUBLICATIONS

International Type Search Report for International Application No. AU2015902393, Search completed May 16, 2016, Mailed May 16, 2016, 8 pgs.

Islam et al., "Methods for artifact detection and removal from scalp EEG: A review," Neurophysiologie Clinique-Clinical Neurophysiology, Oct. 2016, 46(4): 287-305.

Jang et al, "Single Channel Signal Separation Using Time-Domain Basis Functions," IEEE Signal Processing Letters, Jun. 2003, vol. 10, No. 6, 13 pgs.

Jang et al., "A Maximum Likelihood Approach to Single-channel Source Separation," Journal of Machine Learning Research, Dec. 2003, vol. 4, pp. 1365-1392.

Japanese Office Action for Application No. 2017-546830, Mailed Feb. 20, 2020, 5 pages with English translation.

Japanese Office Action for Application No. 2017-553090, Mailed Mar. 16, 2020, 12 pages with English translation.

Japanese Office Action for Application No. 2018-552138, Mailed Mar. 1, 2021, 7 pages with English translation.

Japanese Office Action for Application No. 2018-513699, Mailed Jun. 8, 2020, 7 pages with English translation.

Jeffrey et al., "A reliable method for intracranial electrode implantation and chronic electrical stimulation in the mouse brain", BMC Neuroscience. Biomed Central. London, GB. vol. 14. No. 1, Aug. 6, 2013 (Aug. 6, 2013), pp. 1-8.

Jones et al., "Scaling of Electrode- Electrolyte Interface Model Parameters In Phosphate Buffered Saline," IEEE Transactions on Biomedical Circuits and Systems, 2015, vol. 9, No. 3, pp. 441-448, DOI:10.1109/TBCAS.2014.4223759.

Kent et al., "Instrumentation to Record Evoked Potentials for Closed-Loop Control of Deep Brain Stimulation", Conf. Proc. IEEE Eng. Med Biol. Sol, Aug. 2012, 10 pgs.

Kent et al., AR "Recording evoked potentials during deep brain stimulation: development and validation of instrumentation to suppress the stimulus artefact", J Neural Eng. Jun. 2012; 9(3):036004, Apr. 18, 2012. doi:10.1088/ 1741-2560/9/3/036004.

Kent, "Characterization of Evoked Potentials During Deep Brain Stimulation in the Thalamus", Dissertation, Duke University. Retrieved from https://hdl.handle.net/10161/8195, 2013.

Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.

Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi: 10.1016/S0306-4522 (98)00022-0.

Kopelman et al., "Attempted Reversible Sympathetic Ganglion Block by an Implantable Neurostimulator", Interactive Cardiovascular and Thoracic Surgery, Feb. 7, 2012, vol. 14, Issue 5, pp. 605-609.

Krames et al., "Neuromodulation", 1st Edition, Academic Press, 2009, p. 540-541.

Krarup, Christian "Compound sensory action potential in normal and pathological human nerves", Muscle & nerve, vol. 29, No. 4 (2004), pp. 465-483.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Neurology, 53, No. 4, 1999, pp. 871-874.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Laird et al., "A Model of Evoked Potentials in Spinal Cord Stimulation, "Annu Int Conf IEEE Eng Med Biol Soc. 2013;2013:6555-8. doi: 10.1109/EMBC.2013.6611057 (abstract only).

Laird-Wah, "Improving Spinal Cord Stimulation: Model-Based Approaches to Evoked Response Telemetry," UNSW Thesis, Aug. 2015, 279 pgs.

Lempka, Scott "The Electrode-Tissue Interface During Recording and Stimulation in the Central Nervous System", published on May 2010.

Levy et al., "Incidence and Avoidance of Neurologic Complications with Paddle Type Spinal Cord Stimulation Leads", Neuromodulation 14(15), Sep. 2011, pp. 412-422.

Li, S. et al., "Resonant antidromic cortical circuit activation as a consequence of high-frequency subthalamic deep-brain stimulation", J Neurophysiol. Dec. 2007; 98(6): 3525-37. First published Oct. 10, 2007. doi: 10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi: 10.1152/jn.00855.2002.

Macefield, "Spontaneous and Evoked Ectopic Discharges Recorded from Single Human Axons", Muscle & Nerve 21, No. 4, Apr. 1998, pp. 461-468.

Mah Nam et al., "Measurement of the current-distance relationship using a novel refractory interaction technique", J. Neural Eng. 6(2): 036005, published May 20, 2009, 22 pgs.

Mannan et al., "Identification and Removal of Physiological Artifacts From Electroencephalogram Signals: A Review," IEEE Access, May 31, 2018, vol. 6, pp. 30630-30652, https://doi.org/10.1109/ACCESS.2018.2842082.

Markandey, Vishal "ECG Implementation on the TMS320C5515 DSP Medical Development Kit (MOK)", Texas Instruments Application Report Jun. 2010, 35 pgs.

Massachusetts Institute of Technology, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.

Matzner et al., "Na+ Conductance and the Threshold for Repetitive Neuronal Firing", Brain Research 597, No. 1 (Nov. 27, 1992): pp. 92-98, doi: 10.1016/0006-8993(92)91509-D.

McGill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.

Medtronic, RestoreSensor Neurostimulator, Retrieved from: http://web.archive.org/web/20150328092923/http://professional.medtronic.com:80/pt/neuro/scs/prod/restore-sensor/features-specifications/index.htm,, Capture Date Jul. 9, 2012, Printed on May 11, 2017.

Medtronic, Spinal Cord Stimulation, RestoreSensor Neurostimulator, Features and Specification: Specification, Printed Jun. 16, 2014, 2 pgs.

Medtronic, Spinal Cord Stimulation, RestoreSensor Neurostimulator, Features and Specification: Summary Printed Jun. 16, 2014, 1 pg.

Melzack et al., "Pain mechanisms: a new theory", Science, New York, New York, vol. 150, No. 3699, Nov. 19, 1965, pp. 971-979.

Miles et al., "An Electrode for Prolonged Stimulation of the Brain", Proc. 8th Meeting World Soc. Stereotactic and Functional Neurosurgery, Part Ill, Zurich, 1981, Appl. Neurophysiol, 45, 1982, pp. 449-445.

Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.

Niazy et al., "Removal of FMRI environment artifacts from EEG data using optimal basis sets," Neurolmage, 2005, vol. 28, pp. 720-737, available online Sep. 16, 2005, doi:10.1016/j.neuroimage.2005.06.0607.

(56) References Cited

OTHER PUBLICATIONS

Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.

North et al., "Prognostic value of psychological testing in patients undergoing spinal cord stimulation: a prospective study," Neurosurgery, Aug. 1, 1996, vol. 39, Issue 2, pp. 301-311, https://doi.org/10.1097 /00006123-199608000-00013.

Oakley et al., "Spinal Cord Stimulation: Mechanisms of Action", Spine 27, No. 22, Nov. 15, 2002, pp. 257 4-2583.

Oakley et al., "Transverse Tripolar Spinal Cord Stimulation: Results of an International Multicenter Study", Neuromodulation, vol. 9, No. 3, 2006, pp. 192-203.

Obradovic et al., "Effect of pressure on the spinal cord during spinal cord stimulation in an animal model", Poster, 18th Annual Meeting of the North American Neuromodulation Society, Dec. 11-14, 2014, Las Vegas.

Office Action for Chinese Patent Application No. 201680020725.4, dated Mar. 16, 2020, 8 pgs.

Oh et al., "Long-term hardware-related complications of deep brain stimulation", Neurosurgery, vol. 50, No. 6, Jun. 2002, pp. 1268-1274, discussion pp. 1274-1276.

Olin et al., "Postural Changes in Spinal Cord Stimulation Perceptual Thresholds", Neuromodulation, vol. 1 , No. 4, 1998, pp. 171-175.

Opsommer, E. et al. "Determination of Nerve Conduction Velocity of Cfibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.

Orsta Vik, Kristin et al. "Pathological C-fibres in patients with a chronic painful condition", Brain (2003), 126, 567-578.

Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.

Parker et al., "Closing the Loop in Neuromodulation Therapies: Spinal Cord Evoked Compound Action Potentials During Stimulation for Pain Management (230).", 2011, in 15th Annual Meeting, North American Neuromodulation Society (p. 48). Presented at the North American Neuromodulation Society, Las Vegas.

Parker et al., Compound Action Potentials Recorded in the Human Spinal Cord During Neurostimulation for Pain Relief, Pain, vol. 153, 2012, pp. 593-601.

Parker et al., "Electrically Evoked Compound Action Potentials Recorded From the Sheep Spinal Cord", Neuromodulation, vol. 16, 2013, pp. 295-303.

Parker et al., "Compound Action Potentials Recorded in the Human Spinal Cord During Neurostimulation for Pain Relief," Pain, vol. 153, 2012, pp. 593-60 (abstract only).

Parker et al.., "Electrically Evoked Compound Action Potentials Recorded from the Sheep Spinal Cord," Neuromodulation, Published Jul. 11, 2013, 16(4):295-303; discussion 303. doi:10.1111/ner.12053 (abstract only).

Partial European Search Report for European Application No. 16775966.1, Search completed Oct. 26, 2018, Mailed Nov. 6, 2018, 11 Pgs.

Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.

Peterson et al., "Stimulation artifact rejection in closed-loop, distributed neural interfaces," ESSCIRC, 42nd European Solid-State Circuits Conference, Lausanne,2016, pp. 233-236.

Rattay, "Analysis of Models for External Stimulation of Axons", IEEE Transactions on Biomedical Engineering, vol. BME-33, No. 10, Oct. 1986, pp. 974-977.

Richter et al., "EMG and SSEP Monitoring During Cervical Spinal Cord Stimulation", Journal of Neurosurgical Review 2011, Southern Academic Press, 1(S1), 2011, pp. 61-63.

Ridder et al., "Burst Spinal Cord Stimulation for Limb and Back Pain", World Neurosurgery, 2013, 9 pgs.

Rijkhoff et al., "Acute Animal Studies on the Use of Anodal Block to Reduce Urethral Resistance in Sacral Root Stimulation," IEEE Transactions on Rehabilitation Engineering, 1994, vol. 2, No. 2, pp. 92-99.

Rijkhoff et al., "Orderly Recruitment of Motoneurons in an Acute Rabbit Model, " Annual International Conference of the IEEE Engineering in Medicine and Biology Society, 1998, vol. 20, No. 5, pp. 2564-2565.

Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.

Roy, S. H. et al., "Effects of Electrode Location on Myoelectric Conduction Velocity and Median Frequency Estimates", J. Appl. Physiol. 61 (4), 1986, pp. 1510-1517.

Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.

Schmidt et al., "Gating of tactile input from the hand", Exp Brain Res, 1990, 79, pp. 97-102.

Scott et al., "Compact nonlinear model of an implantable electrode array for spinal cord stimulation (SCS)," IEEE Trans Biomed Circuits Syst. Jun. 2014;8(3):382-90. doi: 10.1109/TBCAS.2013.2270179 (abstract only).

Scott et al., "Compact Nonlinear Model of an Implantable Electrode Array for Spinal Cord Stimulation (SCS)," IEEE Transactions on Biomedical Circuits and Systems, 2014, vol. 8, No. 3, pp. 382-390.

Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130, ISSN: 0148-396X; Accession: 00006123-199412000-00016;.

Siegfried et al., "Intracerebral Electrode Implantation System", Journal of Neurosurgery, vol. 59, No. 2, Aug. 1983, pp. 356-3591.

Srinivasan, S "Electrode/Electrolyte Interfaces: Structure and Kinetics of Charge Transfer", Fuel Cells, 2006, Chapter 2, 67 Pages.

Stanslaski et al., "Design and Validation of a Fully Implantable, Chronic, Closed-Loop Neuromodulation Device with Concurrent Sensing and Stimulation," IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.

Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.

Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.

Struijk, "The Extracellular Potential of a Myelinated Nerve Fiber in an Unbounded Medium and in Nerve Cuff Models", Biophysical Journal vol. Jun. 1, 72997 2457-2469.

Sufka et al., "Gate Control Theory Reconsidered", Brain and Mind, 3, No. 2, 2002, pp. 277-290.

Takahashi et al, "Classification of neuronal activities from tetrode recordings using independent component analysis, " Neurocomputing, (2002), vol. 49, Issues 1-4, pp. 289-298.

Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi: 10.1016/j.clinph.2006.07.309.

Tasker, "Deep Brain Stimulation is Preferable to Thalamotomy for Tremor Suppression", Surgical Neurology, 49, No. 2, 1998, pp. 145-153.

Taylor et al., "Spinal Cord Stimulation for Chronic Back and Leg Pain and Failed Back Surgery Syndrome: A Systematic Review and Analysis of Prognostic Factors", Spine, vol. 30, No. 1, 2004, pp. 152-160.

(56) References Cited

OTHER PUBLICATIONS

Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tronnier et al., "Magnetic Resonance Imaging with Implanted Neurostimulators: An In Vitro and In Vivo Study", Jan. 1999, Neurosurgery, vol. 44(1), pp. 118-125 (Year: 1999).
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T. "Laminectomy versus Percutaneous Electrode Placement for Spinal Cord Stimulation," Neurosurgery, vol. 46 (2), Feb. 2000, pp. 399-405.
Vleggeert et al., Lan Kamp "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blockingout-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Written Opinion for International Application No. PCT/AU2012/000511, International Filing Date May 11, 2012, Search Completed May 17, 2012, Mailed May 18, 2012, 5 pgs.
Written Opinion for International Application No. PCT/AU2012/000512, International Filing Date May 11, 2012, Search Completed Jul. 10, 2012, Mailed Jul. 11, 2012, 7 pgs.
Written Opinion for International Application No. PCT/AU2012/000513, International Filing Date May 11, 2012, Search Completed May 29, 2012, Mailed May 30, 2012, 10 pgs.
Written Opinion for International Application No. PCT/AU2012/000515, International Filing Date May 11, 2012, Search Completed May 21, 2012, Mailed Jun. 4, 2012, 4 pgs.
Written Opinion for International Application No. PCT/AU2012/000516, International Filing Date May 11, 2012, Search Completed Jul. 11, 2012, Mailed Jul. 12, 2012, 8 pgs.
Written Opinion for International Application No. PCT/AU2012/000517, International Filing Date May 11, 2012, Search Completed Jun. 4, 2012, Mailed Jun. 6, 2012, 5 pgs.
Written Opinion for International Application No. PCT/AU2012/000518, International Filing Date May 11, 2012, Search Completed Jun. 8, 2012, Mailed Jun. 12, 2012, 10 pgs.
Wu et al., "Changes in A13 Non-nociceptive Primary Sensory Neurons in a Rat Model of Osteoarthritis Pain", Molecular Pain 6, No. 1 (Jul. 1, 2010): 37, doi: 10.1186/17 44-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yamada et al., "Extraction and Analysis of the Single Motor Unit F-Wave of the Median Nerve", EMG Methods for Evaluating Muscle and Nerve Function, InTech, 2012, 15 pgs.
Yearwood, T. L. "Pulse Width Programming in Spinal Cord Stimulation: a Clinical Study", Pain Physician. 2010. Vol. 13, pp. 321-335.
Yingling et al., "Use of Antidromic Evoked Potentials in Placement of Dorsal Cord Disc Electrodes", Applied Neurophysiology, 1986, vol. 49, pp. 36-41.
Yuan, S. et al. "Recording monophasic action potentials using a platinumelectrode ablation catheter", Europace. Oct. 2000; 2(4):312-319.
Zhang et al., "Automatic Artifact Removal from Electroencephalogram Data Based on a Priori Artifact Information," BioMed Research International, Aug. 25, 2015, Article ID 720450, 8 pgs., DOI: https://doi.org/10.1155/2015/720450.
Zhou et al., "A High Input Impedance Low Noise Integrated Front-End Amplifier for Neural Monitoring," IEEE Transactions on Biomedical Circuits and Systems, 2016, vol. 10, No. 6, pp. 1079-1086.

| With feedback compared to Without feedback | Pain Relief | | | | |
|---|---|---|---|---|---|
| | Much worse | Somewhat worse | No difference | Somewhat better | Much better |
| Side Effects — Much more | | | | | |
| Somewhat more | | | | | |
| No difference | | | 1 | | |
| Somewhat less | | | 3 | 2 | 1 |
| Much less | | | 1 | | |

METHOD AND DEVICE FOR FEEDBACK CONTROL OF NEURAL STIMULATION

CROSS-REFERENCE TO RELATED APPLICATIONS

This application is a continuation of U.S. patent application Ser. No. 17/724,652, filed Apr. 20, 2022, which is a continuation of U.S. patent application Ser. No. 17/532,725, filed Nov. 22, 2021 and issued on May 31, 2022 as U.S. Pat. No. 11,344,729, which is a continuation of U.S. patent application Ser. No. 16/669,393, filed Oct. 30, 2019 and issued on Jan. 11, 2022 as U.S. Pat. No. 11,219,766, which is a continuation of U.S. patent application Ser. No. 15/535,008, filed Jun. 9, 2017 and issued on Dec. 10, 2019 as U.S. Pat. No. 10,500,399, which is a national stage of Application No. PCT/AU2015/050787, filed Dec. 11, 2015, which application claims the benefit of Australian Provisional Patent Application No. 2014905031, filed Dec. 11, 2014, the disclosures of each of which are incorporated herein by reference in their entireties.

TECHNICAL FIELD

The present invention relates to controlling a neural response to a stimulus, and in particular relates to measurement of a compound action potential by using one or more electrodes implanted proximal to the neural pathway, in order to provide feedback to control subsequently applied stimuli.

BACKGROUND OF THE INVENTION

There are a range of situations in which it is desirable to apply neural stimuli in order to give rise to a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at a frequency in the range of 30 Hz-100 Hz.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. Depending on the polarity of sense electrodes the CAP equivalently may present in the measurement with the opposite polarity, in which case the nomenclature N1-P1-N2 is used. In either case this is caused by the region of activation passing the recording electrode as the action potentials propagate along the individual fibres. An observed CAP signal will typically have a maximum amplitude in the range of microvolts, whereas a stimulus applied to evoke the CAP is typically several volts.

Conventionally, spinal cord stimulation (SCS) delivers stimulation to the dorsal column at a fixed current. When a subject moves or changes posture the distance between the spinal cord and the implanted lead varies, resulting in an increase or decrease in the amount of current received by the dorsal columns. These changes in current result in changes to recruitment and paresthesia, which can reduce the therapeutic effect of SCS and can create side effects including over-stimulation.

If a stimulus is of an amplitude and/or peak width and/or has other parameter settings which put it below the recruitment threshold, delivery of such a stimulus will fail to recruit any neural response. Thus, for effective and comfortable operation, it is necessary to maintain stimuli amplitude or delivered charge above the recruitment threshold. It is also necessary to apply stimuli which are below a comfort threshold, above which uncomfortable or painful percepts arise due to increasing recruitment of Aδ fibres which are thinly myelinated sensory nerve fibres associated with joint position, cold and pressure sensation. In almost all neuromodulation applications, a single class of fibre response is desired, but the stimulus waveforms employed can recruit action potentials on other classes of fibres which cause unwanted side effects, such as muscle contraction if motor fibres are recruited. The task of maintaining appropriate stimulus amplitude is made more difficult by electrode migration and/or postural changes of the implant recipient, either of which can significantly alter the neural recruitment arising from a given stimulus, depending on whether the stimulus is applied before or after the change in electrode position or user posture. Postural changes alone can cause a comfortable and effective stimulus regime to become either ineffectual or painful.

Another control problem, facing neuromodulation systems of all types, is achieving neural recruitment at a sufficient level required for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides an automated method of controlling a neural stimulus, the method comprising:

applying the neural stimulus to a neural pathway in order to give rise to an evoked action potential on the neural pathway, the stimulus being defined by at least one stimulus parameter;

measuring a neural compound action potential response evoked by the stimulus, and deriving from the measured evoked response a feedback variable;

completing a feedback loop by using the feedback variable to control the at least one stimulus parameter value; and adaptively compensating for changes in a gain of the feedback loop caused by electrode movement relative to the neural pathway.

According to a second aspect the present invention provides an implantable device for controllably applying a neural stimulus, the device comprising:

a plurality of electrodes including one or more nominal stimulus electrodes and one or more nominal sense electrodes;

a stimulus source for providing a stimulus to be delivered from the one or more stimulus electrodes to a neural pathway in order to give rise to an evoked action potential on the neural pathway;

measurement circuitry for recording a neural compound action potential signal sensed at the one or more sense electrodes; and a control unit configured to:
control application of a neural stimulus as defined by at least one stimulus parameter;
measure via the measurement circuitry a neural compound action potential response evoked by the stimulus;
determine from the measured evoked response a feedback variable;
complete a feedback loop by using the feedback variable to control the at least one stimulus parameter value; and
adaptively compensate for changes in a gain of the feedback loop caused by electrode movement relative to the neural pathway.

According to a third aspect the present invention provides a non-transitory computer readable medium for controllably applying a neural stimulus, comprising the following instructions for execution by one or more processors:

computer program code means for applying the neural stimulus to a neural pathway in order to give rise to an evoked action potential on the neural pathway, the stimulus being applied as defined by at least one stimulus parameter;

computer program code means for measuring a neural compound action potential response evoked by the stimulus and deriving from the measured evoked response a feedback variable;

computer program code means for completing a feedback loop by using the feedback variable to control the at least one stimulus parameter value; and computer program code means for adaptively compensating for changes in a gain of the feedback loop caused by electrode movement relative to the neural pathway.

The present invention recognises that (i) recruitment of evoked compound action potentials upon the neural pathway by a given stimulus will vary based on the distance of the stimulus electrode(s) from the neural pathway, and (ii) the observed amplitude of a given ECAP upon the neural pathway will vary based on the distance of the sense electrode(s) from the neural pathway, so that electrode movement as may be caused by patient movement, postural changes, heartbeat or the like will affect the feedback loop gain of a system using feedback control of the stimulus.

In some embodiments of the invention, adaptively compensating for changes in the feedback loop may comprise maintaining a corner frequency of the feedback loop at a desired value or within a desired range. For example the desired value or range of the corner frequency may be selected to suitably attenuate low frequency noise such as heartbeat as well as high frequency noise such as electrical amplifier noise. Moreover, in some embodiments, the desired value or range of the corner frequency may be selected to bias attenuation of heartbeat and noise while the recipient is in a more or most sensitive posture, as compared to when the recipient is in a less sensitive posture, sensitive postures being those with a steeper slope of an ECAP growth curve.

In some embodiments of the invention the feedback loop could be a first order feedback loop. Alternatively, the feedback loop could be a second order feedback loop, or higher order feedback loop.

In some embodiments the feedback loop is further configured to adaptively compensate for electrical noise, such as amplifier noise, EMG noise, and neural activity not evoked by the implant.

Some embodiments of the present invention recognise that a slope P of the ECAP growth curve varies with the distanced of the electrode array from the nerve fibre or fibres, so that P is some function of d. Such embodiments of the present invention also recognise that the stimulus threshold T, being the minimum stimulus current at which a neural response will be evoked, also varies with d, so that T is some function of d.

In such embodiments, the slope P can be expressed as a function of T. While d is difficult to determine precisely and is thus often an unknown, T and P can be regularly or substantially continuously measured or estimated by applying stimuli of varying amplitude to explore the slope P of the ECAP amplitude growth and determine a zero intercept, i.e., the threshold T, at any given time.

In some such embodiments, an estimation unit may be provided which produces an estimate $P'$ of the slope P. The estimation $P'$ may in some embodiments be produced by the estimation unit from an empirical relationship of stimulus current to measured ECAP amplitude, and for example may be estimated as $P'=(V+K)/I$, where V is ECAP amplitude, K is a constant or function which relates P to a stimulus threshold T, for example $K=P.T$, and I is stimulus current amplitude. In such embodiments, the estimate $P'$ may then be introduced into the feedback loop to counteract the effect of P. For example, an error signal of the feedback loop may be scaled by $1/P'$.

The feedback variable could in some embodiments be any one of: an amplitude; an energy; a power; an integral; a signal strength; or a derivative, of any one of: the whole evoked compound action potential; the fast neural response for example in the measurement window 0-2 ms after stimulus; the slow neural response for example in the measurement window 2-6 ms after stimulus; or of a filtered version of the response. The feedback variable could in some embodiments be an average of any such variable determined over multiple stimulus/measurement cycles. The feedback variable may in some embodiments be the zero intercept, or the slope, of a linear portion of the response of Aβ amplitude to varying stimulus current. In some embodiments the feedback variable may be derived from more than one of the preceding measures.

The control variable, or stimulus parameter, could in some embodiments be one or more of the total stimulus charge, stimulus current, pulse amplitude, phase duration, interphase gap duration or pulse shape, or a combination of these.

The present invention thus recognises that using a feedback loop to maintain a constant ECAP is a difficult task as changes in patient posture both create signal inputs and change the loop characteristics. Choosing an optimum corner frequency for the loop is a tradeoff between obtaining optimum noise rejection and optimum loop speed. This tradeoff is made more challenging with variations in loop gain.

The set point of the feedback loop may be configured so as to seek a constant value of ECAP amplitude, or may be configured to seek a target ECAP amplitude which changes over time, for example as defined by a therapy map as described in International Patent Application Publication No. WO2012155188 by the present applicant, the content of which is incorporated herein by reference.

BRIEF DESCRIPTION OF THE DRAWINGS

An example of the invention will now be described with reference to the accompanying drawings, in which:

FIG. 17a is a graph showing ECAP amplitude over time during changes in recipient posture, without feedback control, while

DESCRIPTION OF THE PREFERRED EMBODIMENTS

Figure 1:
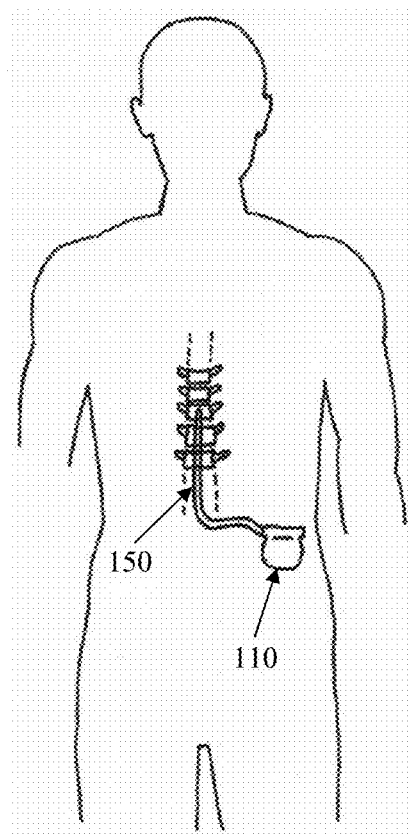
FIG. 1 schematically illustrates an implanted spinal cord stimulator.

FIG. 1 schematically illustrates an implanted spinal cord stimulator 100. Stimulator 100 comprises an electronics module 110 implanted at a suitable location in the patient's lower abdominal area or posterior superior gluteal region, and an electrode assembly 150 implanted within the epidural space and connected to the module 110 by a suitable lead.

Figure 2:
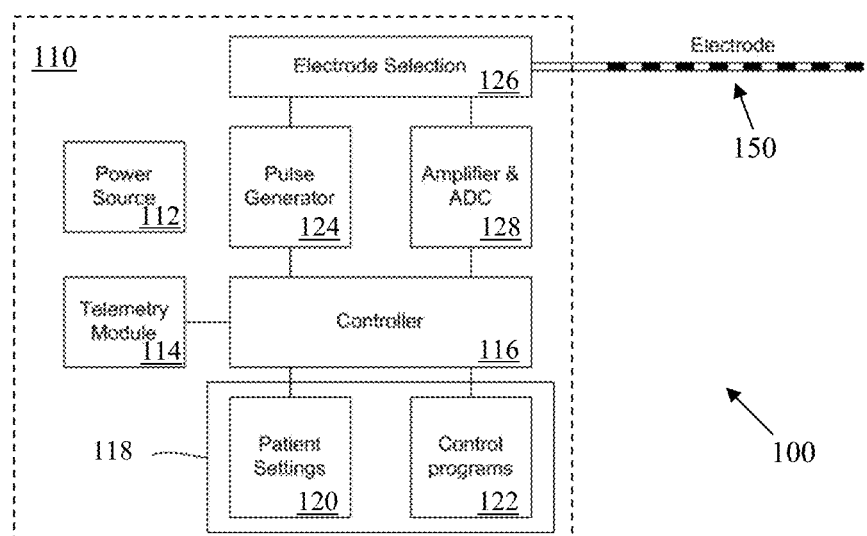
FIG. 2 is a block diagram of the implanted neurostimulator.

FIG. 2 is a block diagram of the implanted neurostimulator 100. Module 110 contains a battery 112 and a telemetry module 114. In embodiments of the present invention, any suitable type of transcutaneous communication, such as infrared (IR), electromagnetic, capacitive and inductive transfer, may be used by telemetry module 114 to transfer power and/or data between an external device and the electronics module 110.

Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode. Measurement circuitry 128 is configured to capture measurements of neural responses sensed at sense electrode(s) of the electrode array as selected by electrode selection module 126.

Figure 3:
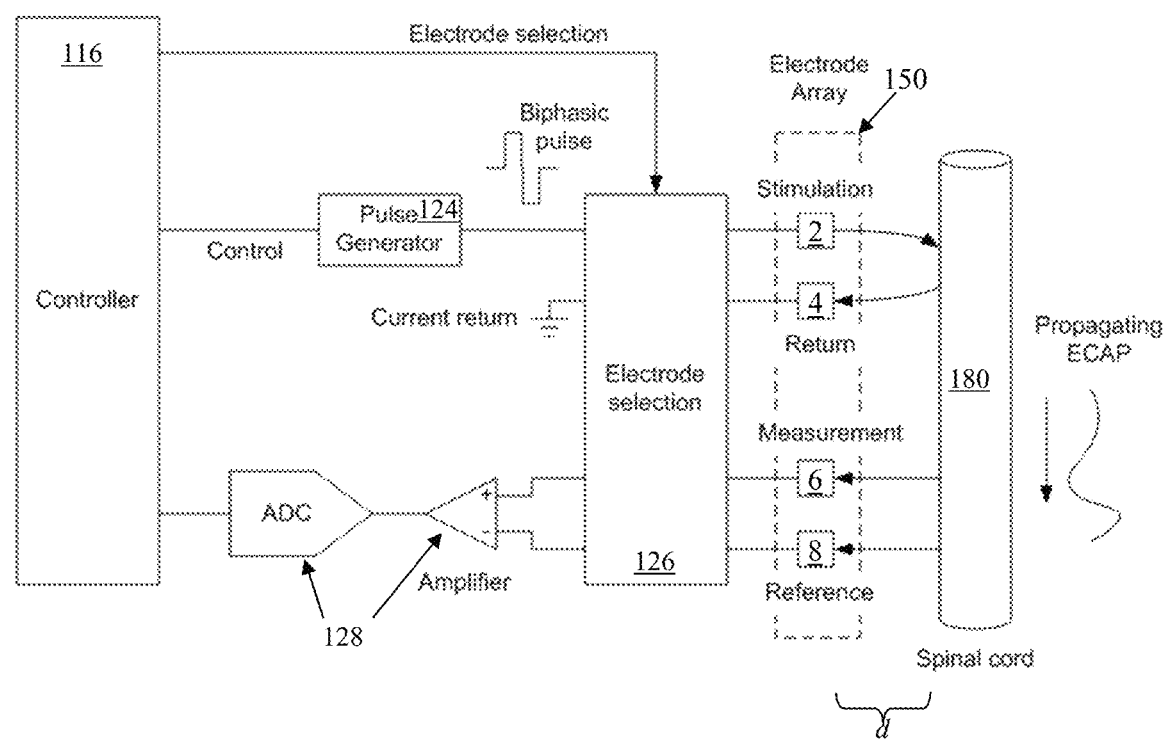
FIG. 3 is a schematic illustrating interaction of the implanted stimulator with a nerve.

FIG. 3 is a schematic illustrating interaction of the implanted stimulator 100 with a nerve 180, in this case the spinal cord however alternative embodiments may be positioned adjacent any desired neural tissue including a peripheral nerve, visceral nerve, parasympathetic nerve or a brain structure. Electrode selection module 126 selects a stimulation electrode 2 of electrode array 150 to deliver an electrical current pulse to surrounding tissue including nerve 180, and also selects a return electrode 4 of the array 150 for stimulus current recovery to maintain a zero net charge transfer.

Delivery of an appropriate stimulus to the nerve 180 evokes a neural response comprising a compound action potential which will propagate along the nerve 180 as illustrated, for therapeutic purposes which in the case of spinal cord stimulator for chronic pain might be to create paraesthesia at a desired location.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry 128, which for example may operate in accordance with the teachings of International Patent Application Publication No. WO2012155183 by the present applicant, the content of which is incorporated herein by reference.

Described below are a number of embodiments of the present invention for optimizing the tradeoff between noise and loop response in the presence of variations in loop gain due to mechanical changes in the electrode-to-nerve distance d.

Figure 4:
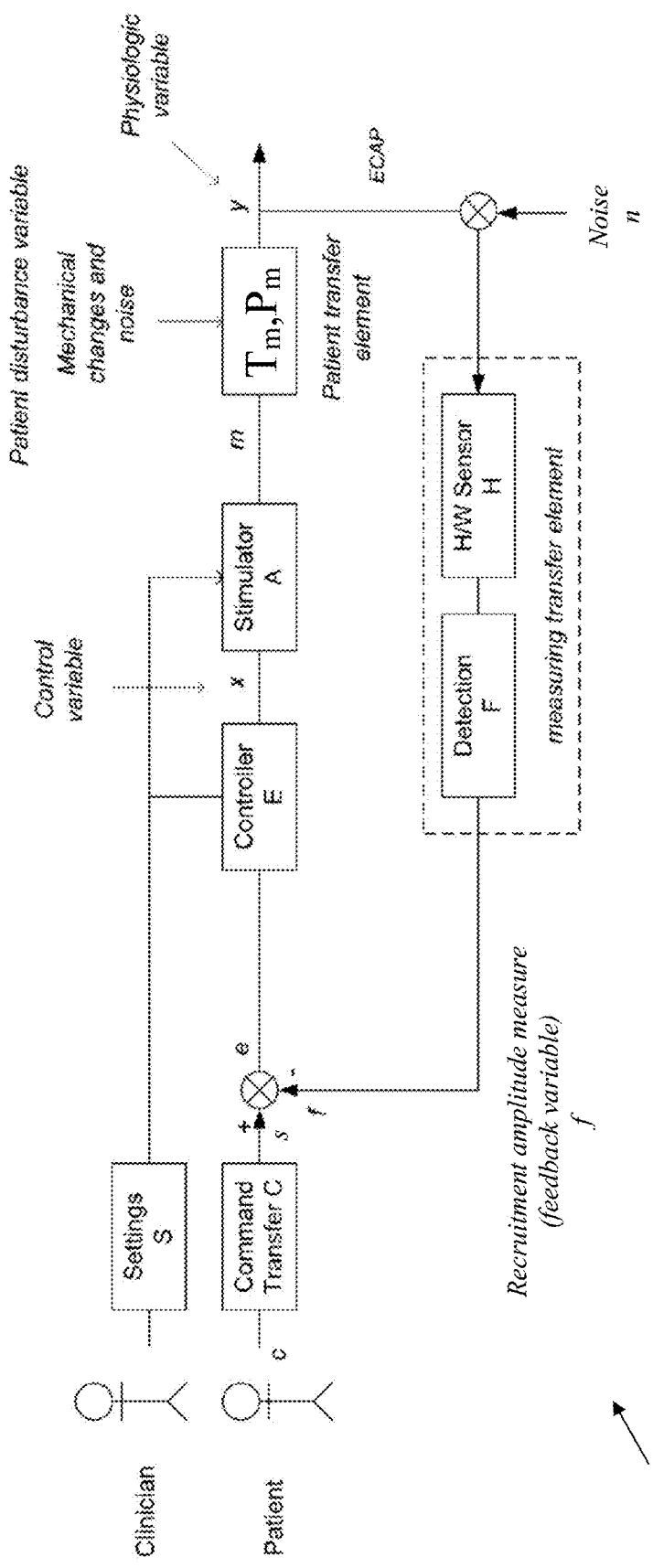
FIG. 4 is a system schematic illustrating elements and inputs of a feedback loop involving the device of FIG. 3, for maintaining neural recruitment at a desired level or upon a desired locus.

Referring to FIG. 4, the feedback loop 400 comprises stimulator A which takes a stimulation current value and converts it into a stimulation pattern defining a pulse width, number of electrodes and the like, to produce an electrical pulse on the stimulation electrodes 2 and 4. In this embodiment the stimulus parameters are: alternating phase on/off, number of phases, number of stimulus electrode poles (bipolar, tripolar etc), pulse width, stimulus position, stimulus to measurement distance, stimulus rate. The stimulation output by stimulator A thus has a summary value m, usually the pulse amplitude, which is controlled by the feedback loop 400.

Figure 5:
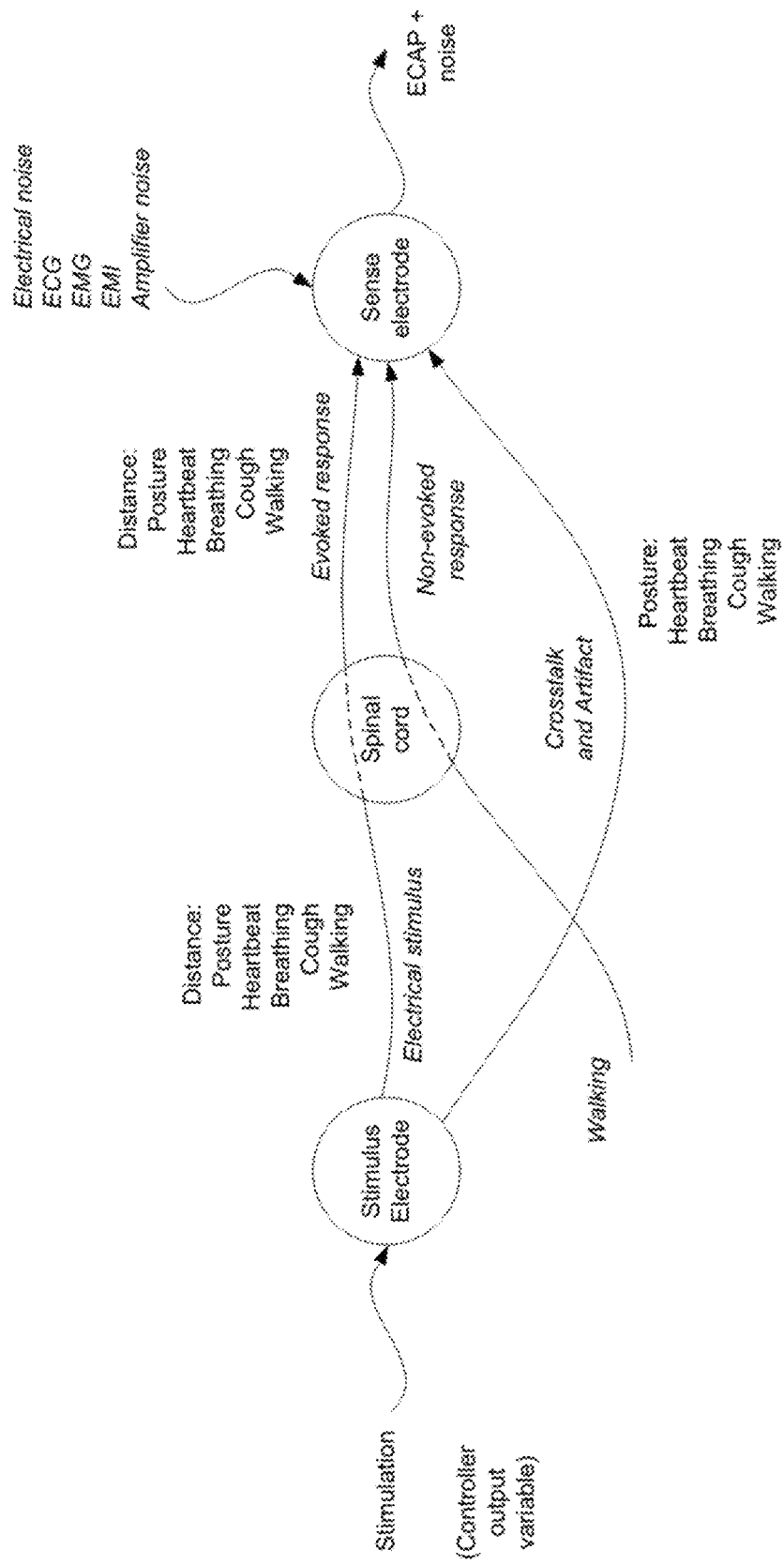
FIG. 5 conceptually illustrates signal interaction in the system of FIGS. 3 and 4.

The stimulus crosses from the electrodes 2,4 to the spinal cord 180. However the neural recruitment arising from this is affected by mechanical changes in d, including posture changes, walking, breathing, heartbeat and so on. The stimulus also generates an evoked response y which may be approximated by the equation y=P(m−T) where T is the stimulus threshold and P is the slope of the response function. Various sources of noise n add to the evoked response y before it is measured, including (a) artifact, which is dependent on both stimulus current and posture; (b) electrical noise from external sources such as 50 Hz mains power; (c) electrical disturbances produced by the body such as neural responses evoked not by the device but by other causes such as peripheral sensory input, ECG, EMG; and (d) electrical noise from amplifiers 128. FIG. 5 conceptually illustrates signal interaction in the system.

The evoked response is amplified in the hardware sensor H then detected by the detector F. The measured evoked response amplitude $f$ is then used as the feedback term for the loop 400, being compared to the setpoint s to produce an error e which is fed to the loop controller E. The feedback term can only be provided to the next stimulus, so there is a net delay of one sample round the loop.

Two clocks (not shown) are used in this embodiment, being a stimulus clock operating at ~60 Hz and a sample clock for measuring the evoked response y operating at ~10 KHz. As the detector is linear, only the stimulus clock affects the dynamics of the feedback loop 400.

The ECAP amplitude $f$ can be used in feedback loop 400 to maintain constant paraesthesia and/or to maintain ECAP amplitude upon a predefined locus configured to allow subjects to receive consistent comfortable stimulation in every posture.

Figure 6:
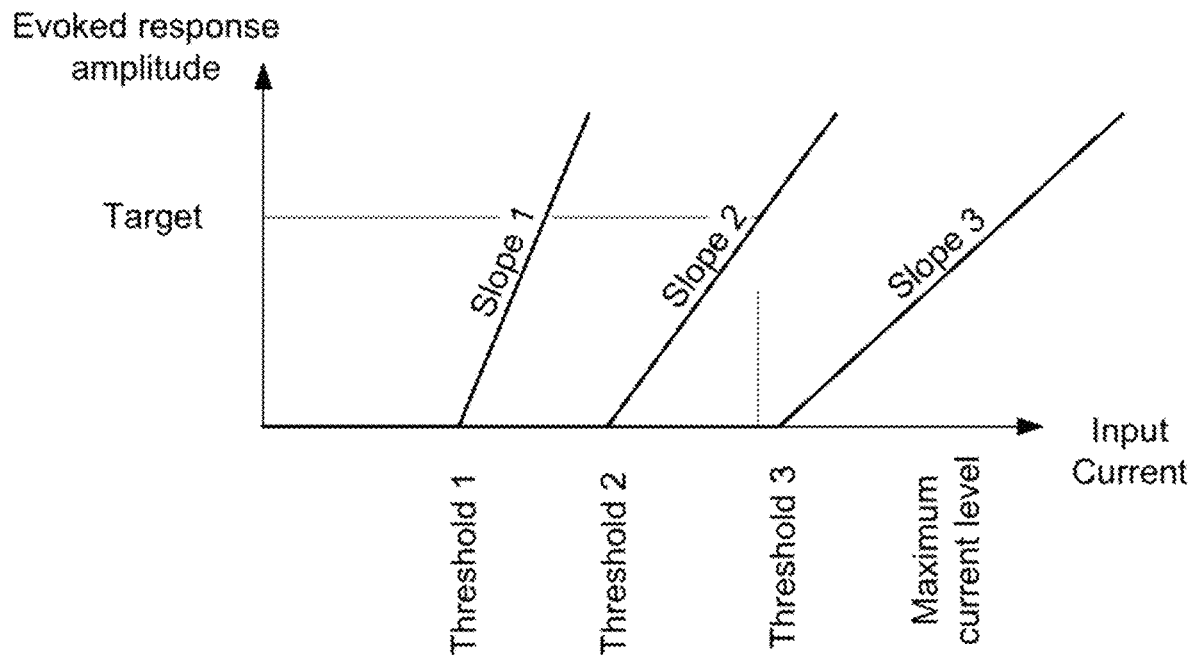
FIG. 6 illustrates the variation in the slope of the growth curve of the ECAP response amplitude, with changing posture.

FIG. 6 illustrates the variation in the slope of the growth curve of the ECAP response amplitude, with changing posture. While only three postures are shown in FIG. 6, the ECAP growth curve for any given posture can lie between or outside the curves shown, on a continuously varying basis depending on posture, with the curve moving at unpredictable times whenever the patient moves or changes posture. Notably, the growth curve changes with posture in a manner whereby the stimulus threshold current changes, as indicated at Threshold 1, Threshold 2, Threshold 3 in FIG. 6, but the slope of the growth curve also changes, as indicated by Slope 1, Slope 2, Slope 3 in FIG. 6. The present invention recognises that at a posture producing a small threshold stimulus current, the growth curve slope will be larger (steeper) while at a posture producing a larger threshold stimulus current, the growth curve slope will be smaller. Thus, the growth curve slope P reduces as threshold T increases. One assumption can be that P=K/T where K is some constant.

Figure 7:
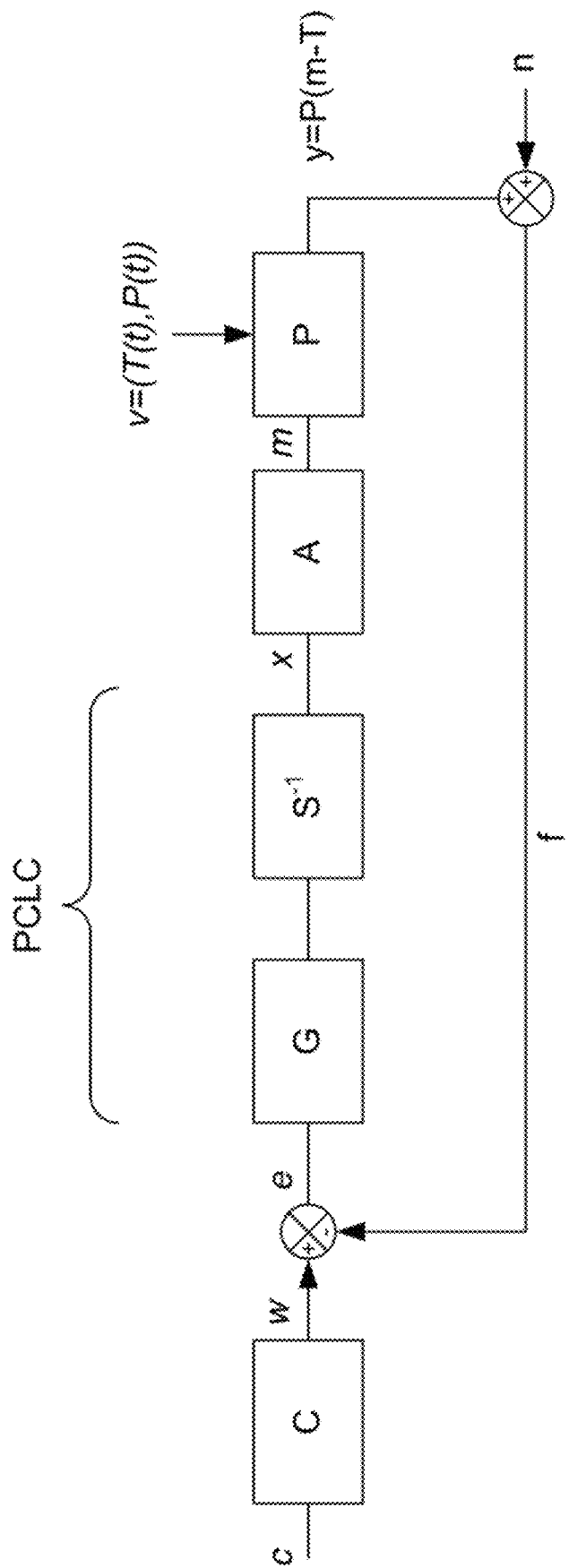
FIG. 7 is a continuous time representation of a first order feedback loop in accordance with one embodiment of the present invention.

In a first embodiment a first order loop transfer function can be formulated in order to provide suitable feedback control in this scenario. FIG. 7 shows the first level of simplification of the loop with a first-order controller. For the purposes of analysis and simulation, there are three inputs: 1. The set point c. Once set, this is left at a single value for long periods. 2. Changes in mechanical state v. This signal input models posture change, heartbeat, breathing etc. Most of these signals have primary components below 2 Hz. 3. Noise n. This consists mainly of amplifier noise, EMG and non-evoked responses.

The requirements of the loop can be summarized as: 1. The gain from c to y must be 1 at DC, i.e. the loop should target its set-point. 2. Minimize y/v. i.e. keep y constant in the presence of mechanical variations. 3. Minimize n/v. i.e. keep the ECAP constant in the presence of electrical noise. For this analysis, artifact is ignored.

The description starts using Laplace transforms as it is easier to predict the behaviour, though the various implementations use the Z transform. FIG. 7 shows a first order loop. The term "G" is a simple constant multiplier. As can be seen, $Y=P(d)(m-T(d))$ The present invention recognises that a perturbation via the input v injects a signal. The injected signal can be estimated from the differential:

$$\frac{dy}{dd} = \frac{dP}{dd}(m-T) + P\frac{dT}{dd}$$

Even though d is unknown this equation is enlightening as, when (m−T)>0 both changes in P and changes in T create an apparent input signal at the patient transfer element.

The present invention recognises that a perturbation via the input v, i.e. the changes in P, also affect the loop in a second way, by changing the loop gain.

Figure 8:
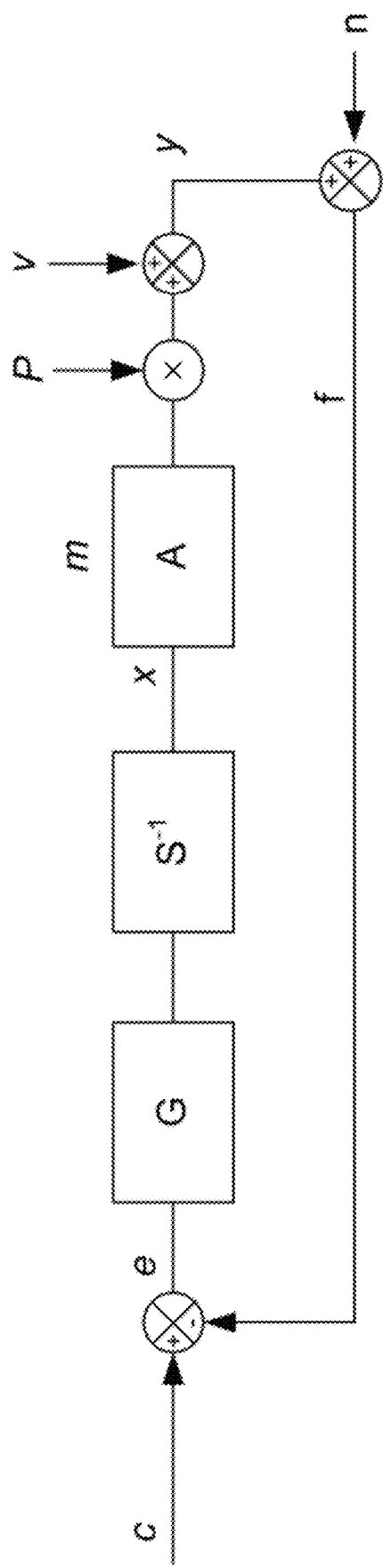
FIG. 8 illustrates the loop of FIG. 7 with simple inputs.
Figure 9:
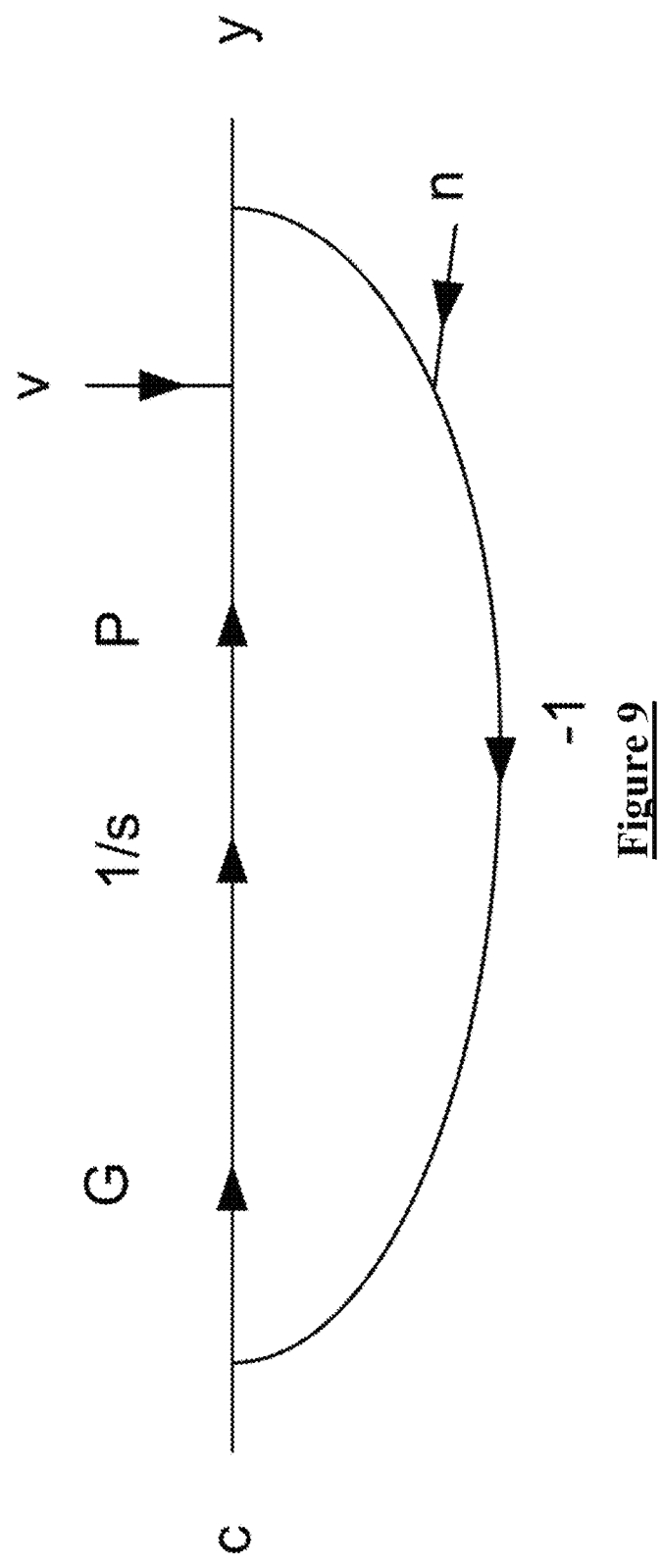
FIG. 9 is a signal flow graph of the continuous time loop with simple inputs of FIG. 8.

For the remainder of this analysis the inputs via the patient transfer element are treated from the point of view of the two separate effects: the input v, which directly affects the output, and the input P, which affects the loop gain but does not form a signal input. FIG. 8 illustrates the continuous time loop with such simplified inputs. FIG. 9 is a signal flow graph of the continuous time loop with simple inputs.

For this analysis, assume A=1, so the transfer function between the target and the ECAP is given by:

$$\frac{y}{c} = \frac{PG}{s + PG}$$

And the transfer function between the input v and the ECAP is given by:

$$\frac{y}{v} = \frac{PGs}{s + PG}$$

Figure 10:
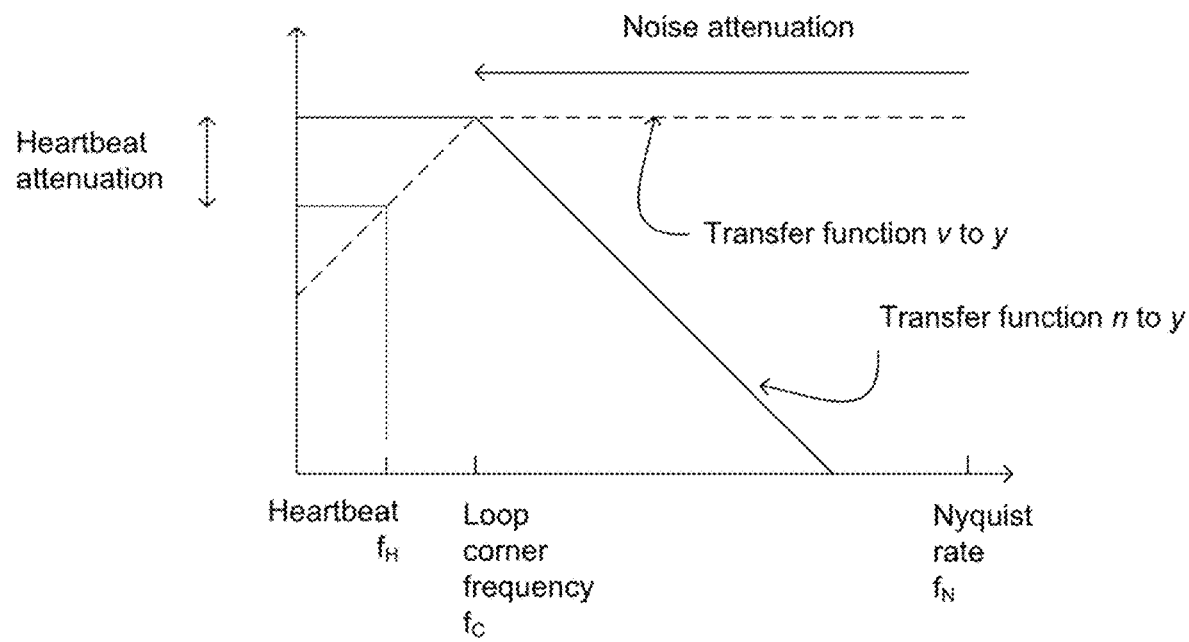
FIG. 10 is a Bode plot of the transfer function of the loop of FIGS. 8-9.

The transfer function can be shown as the Bode plot of FIG. 10, which gives the frequency response specifications. The heartbeat contribution is attenuated by:

$$y/v = f_H/f_C$$

The noise from the amplifier and from non-evoked responses is assumed to be white and is attenuated by:

$$y/n = f_C/f_N$$

Configuring the loop to have a corner frequency between $f_H$ and $f_N$ thus attenuates both noise and heartbeat. The loop is adjusted to have a 3 Hz corner frequency at the most sensitive posture, which typically is when the patient is lying supine. At a sample rate of 60 Hz, this provides around 11 dB of noise and movement attenuation at the heartbeat frequency of one beat per second.

Figure 11:
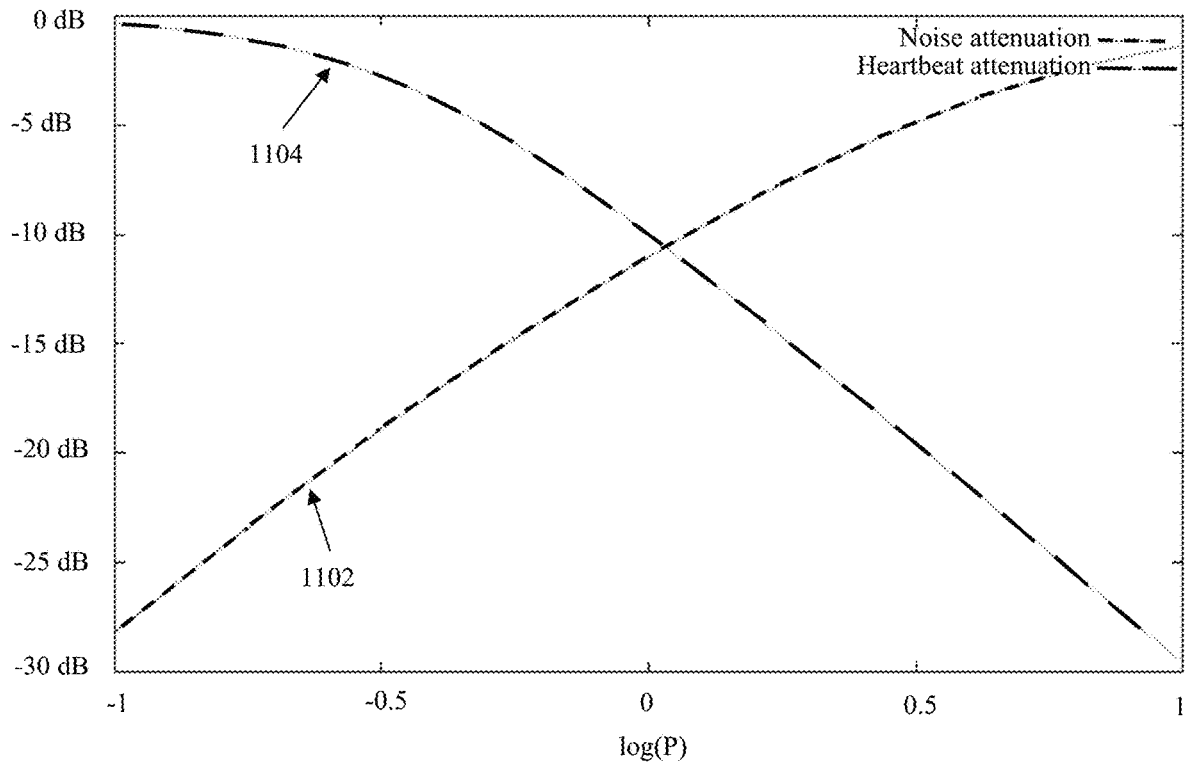
FIG. 11 illustrates variations in attenuation of low frequency heartbeat and high frequency noise, respectively, by the continuous time loop of FIG. 8, in response to changes in recipient posture.

FIG. 11 shows the effect of changes in P upon attenuation of noise (1102) and heartbeat attenuation of heartbeat (1104), by the first order continuous time (Laplace) loop. As the patient changes posture, P changes, and with it the loop corner frequency. This change in noise attenuation is offset by the change in movement attenuation as shown in FIG. 11.

Since P can vary by as much as 10:1, the corner frequency can vary by a similar amount, around 10:1. If P falls sufficiently, a point is reached where the heartbeat is not attenuated. If P rises sufficiently, it reaches a point where noise is not attenuated.

Thus, in this embodiment a fitting procedure to fit the operation of the device 100 to the recipient involves choosing the loop corner frequency at the middle of the range of P values shown in FIG. 11. Since this is affecting a filter characteristic, taking the middle of the range as the geometric mean is preferable to the arithmetic mean.

Figure 12:
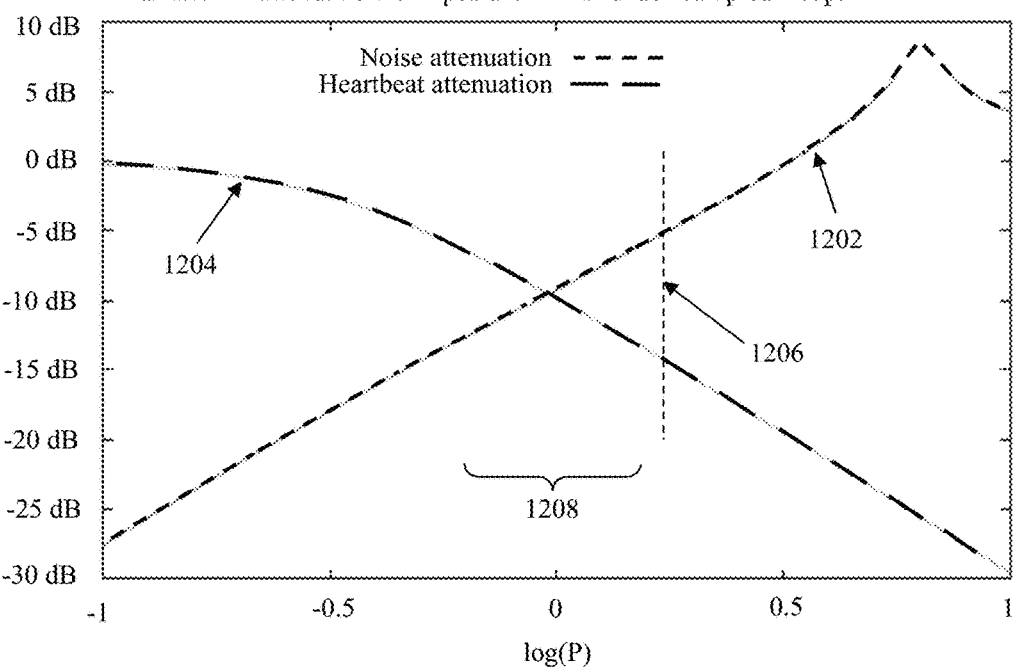
FIG. 12 illustrates variations in attenuation of low frequency heartbeat and high frequency noise, respectively, by a discrete time or sampled data loop equivalent to the continuous time loop of FIG. 8, in response to changes in recipient posture.

The loop of FIGS. 7-11 uses continuous time to aid explanation, however the actual loop, being of a nature which delivers pulsatile stimuli sampled at 10 kHz, involves sampled data. FIG. 12 shows the frequency characteristics of an equivalent sampled data first order loop. In FIG. 12 the more sensitive postures with larger P, such as the recipient lying supine, occur on the right of the plot where log(P)>0. If the loop corner frequency were to be set while the patient was in the least sensitive posture, such as while lying prone, then movement of the person to other postures will move the loop characteristics to the right in FIG. 12, leading to attenuation of noise, and then even amplification of noise noting that curve 1202 is greater than 0 for log(P)>~0.5. Such noise amplification has indeed been observed. Accordingly preferred embodiments fit the device while the recipient is in the most sensitive posture, lying supine. Consequently, as the person moves the loop characteristics move to the left, which results in a reduction in heartbeat attenuation.

In another embodiment, the loop gain may be set while the recipient is in the most sensitive posture, but biased somewhat to the right in FIG. 12 as indicated by 1206 to take more advantage of the central portion 1208 of the response where both heartbeat and noise attenuation are low.

The present invention further recognises that a figure of merit for such feedback loops can be defined, by referring to FIG. 11: Figure of Merit=heartbeat attenuation+noise attenuation, at P=1. This sum remains substantially constant for small variations in posture either side of P=1.

Figure 13:
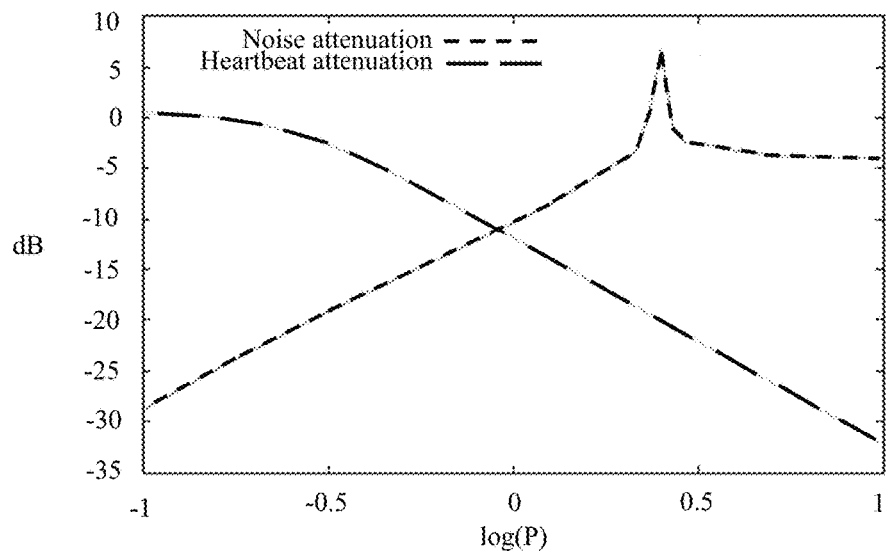
FIG. 13 illustrates variations in attenuation of low frequency heartbeat and high frequency noise, respectively, by a second-order sampled data loop, in response to changes in recipient posture.

FIG. 13 shows the performance of a second-order sampled data loop. Table 1 compares the performance of the first-order continuous, first-order discrete and second order discrete loops, showing that the second order loop performs 3.1 dB better than the first order discrete loop.

TABLE 1

Comparison of loop characteristics

| Loop | Noise | Movement | Figure of Merit (dB) | Improvement compared to 1$^{st}$ Order Discrete | Filter Name |
|---|---|---|---|---|---|
| First order continuous | 11.5 | 9.4 | 20.9 | N/A | sfilterx1 |
| First order discrete | 9.8 | 9.3 | 19.1 | 0 | zfilterx0 |
| Second order discrete | 11.0 | 11.8 | 22.8 | 3.7 | zfilterx8 |

Both the first order and second order sampled data loops amplify noise for P>sqrt(10). The first order loop becomes unstable at P>~5. The second order loop is unstable at P>sqrt(10).

Figure 14:
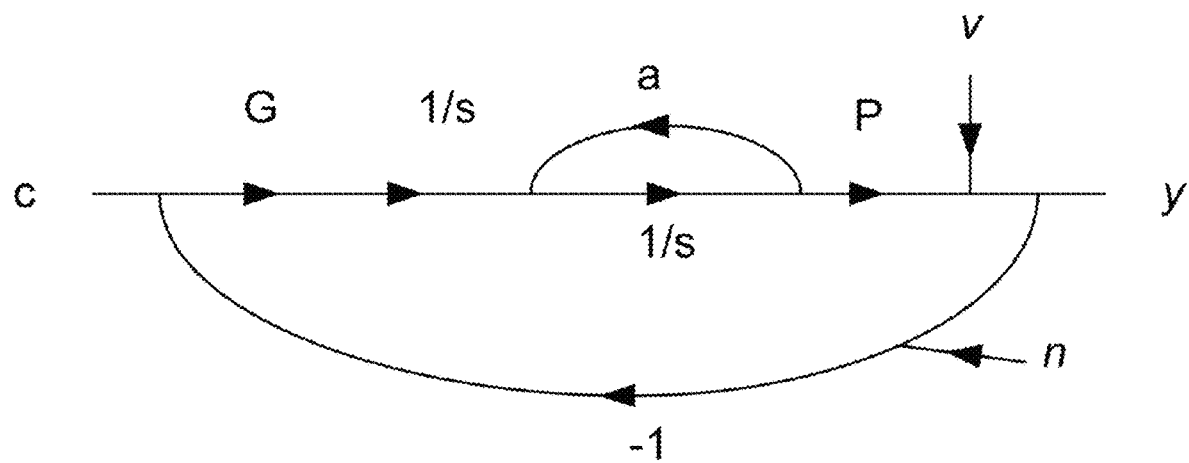
FIG. 14 illustrates a continuous time model of the second order loop reflected in FIG. 13.

The details of implementation of an embodiment comprising a second order loop are now described. In this embodiment a second order filter is designed in the s-domain to aid understanding, then transferred to the z-domain for implementation. FIG. 14 illustrates a continuous time model of the second order loop. This loop of FIG. 14 is used in place of that in FIG. 9, in this embodiment. Its transfer function from noise to output is:

$$\frac{y}{n} = \frac{PG}{s^2 - as + PG}$$

The gain from the patient disturbance to the ECAP:

$$\frac{y}{v} = \frac{PGs(s-a)}{s^2 - as + PG}$$

These are a low-pass and high-pass response respectively. Considering the equation for a second order filter:

$$Gain\,(lpf) = \frac{1}{s^2 - \omega_B s + \omega_0^2}$$

the corner (resonant) frequency is $\omega_o = \pi f_0$ (in radians per second or Hz), so comparing to the equation for the gain from patient disturbance to ECAP, This is critically damped when $\omega_B = 1.414\, \omega_0$. So given P, we can choose G such that:

$$G = \frac{(2\pi f_0)^2}{P}$$

and

The loop was then transformed to the sampled data domain using the bilinear transform to implement each integrator. The bilinear transform approximates a continuous time integrator in the z-domain using the following transfer function, where T is the sample interval.

$$\frac{1}{s} = \frac{T}{2}\frac{z+1}{z-1}$$

Figure 15:
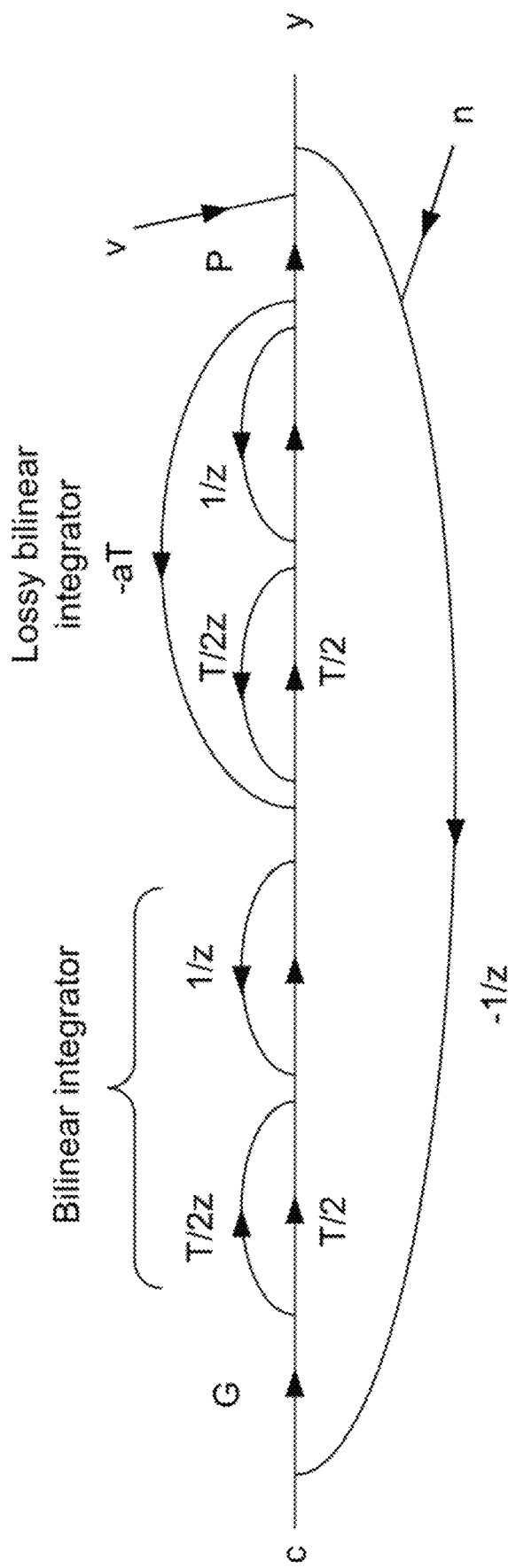
FIG. 15 illustrates the a second order controller in the z-domain, equivalent to the continuous time model of FIG. 14.

FIG. 15 illustrates the equivalent second order controller in the z-domain.

Figure 16:
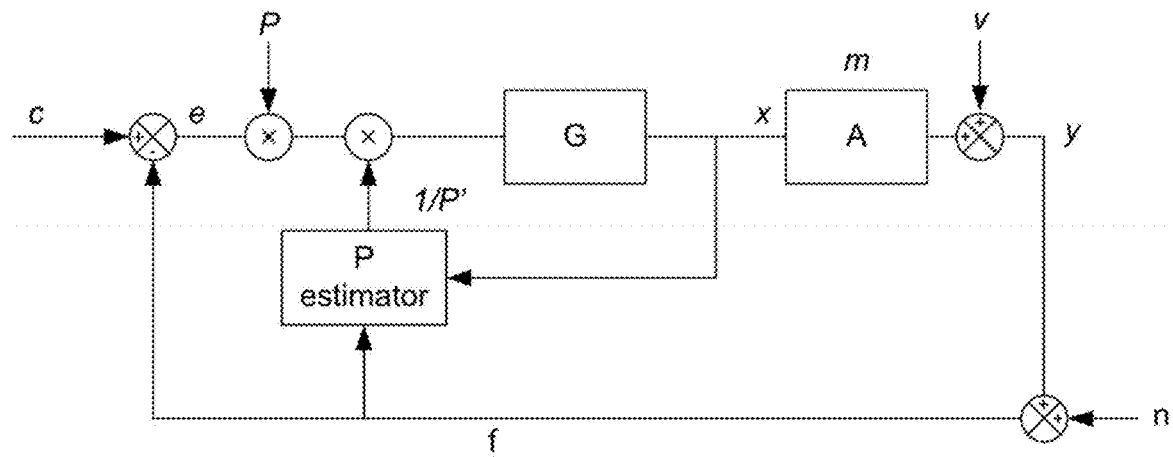
FIG. 16 illustrates a feedback loop comprising P estimation in accordance with another embodiment of the present invention.

Some embodiments may further provide for estimation and compensation for P, as follows. This method estimates P and then using the estimate (P') adjusts the loop gain as shown in FIG. 16. The estimator uses the current value and the measured ECAP amplitude. The method of solving the problem is easier to explain noting that the control variable x is the stimulus current I and the feedback variable $f$ is the measured ECAP voltage V.

The compensation 1/P' is added to the loop at a point where the average signal is zero, so as to perturb the loop as little as possible.

Since both P and T vary with distance to the cord, there must exist a relationship between them. The initial estimation of P uses the empirical relationship, for some K: PT=K. Taking the model of the current growth curve:

$$V = P(I-T)$$

eliminating T and inverting, gives the estimate P':

$$P' = \frac{V+K}{I}$$

To give examples of the method for estimation of K, consider the three patients shown in the following tables.

TABLE 2 patient parameters

| | | Posture 1 (most sensitive) | | | Posture 2 (least sensitive) | | |
|---|---|---|---|---|---|---|---|
| Patient I.D. | Sensitivity ($\mu$V/mA) | Threshold Current (mA) | Comfort Current (mA) | Sensitivity ($\mu$V/mA) | Threshold Current (mA) | Comfort Current (mA) | Variation in P |
| A | 77 | 0.8 | 1 | 26 | 3.7 | 4.5 | 2.96 |
| B | 30 | 2.7 | 4.3 | 20 | 2.9 | 3.7 | 1.50 |
| C | 22 | 4.5 | 10.6 | 19 | 6.1 | 12.6 | 1.16 |

TABLE 3 average values of TP

| TP Most Sensitive | TP Least Sensitive | Average(TP) |
|---|---|---|
| 61.6 | 96.2 | 78.9 |
| 81 | 58 | 69.5 |
| 99 | 115.9 | 107.45 |

TABLE 4

P' estimations of P

| P' Most Sensitive | | P' Least Sensitive | |
|---|---|---|---|
| Comfort | Max | Comfort | Max |
| 94.30 | 90.31 | 22.16 | 22.40 |
| 27.33 | 27.60 | 23.11 | 22.88 |
| 22.80 | 22.70 | 18.33 | 18.40 |

TABLE 5 variation in P/P'

| P/P' Most Sensitive | | P/P' Least Sensitive | | Variation in P/P' |
|---|---|---|---|---|
| 1.22 | 1.17 | 0.85 | 0.86 | 1.44 |
| 0.91 | 0.92 | 1.16 | 1.14 | 0.80 |
| 1.04 | 1.03 | 0.96 | 0.97 | 1.07 |

Thus, tables 2 to 5 show that the P estimator halves the variation in loop gain with P.

The present invention thus recognises that a system using a feedback loop to maintain a constant ECAP is unusual in that the changes in patient posture create both signal inputs and change the loop characteristics. Choosing an optimum corner frequency for the loop is a tradeoff between obtaining optimum noise rejection and optimum loop speed. This tradeoff is made more challenging with variations in loop gain. Methods have been described above that reduce the extent to which loop gain changes with patient posture, allowing for optimum placement of the loop poles. These methods can be used independently or in conjunction.

A study was conducted to examine the effect of posture changes on pain and on side effects (e.g. over-stimulation and under-stimulation), comparing the use of SCS with feedback (automatic current adjustment) against SCS without feedback (conventional fixed current stimulation). Subjects (n=8) were tested with and without feedback control using the Saluda Medical SCS system on the last day of their commercial system trial (5 to 7 days after lead implantation).

With feedback, stimulation current was adjusted automatically by the Saluda system by maintaining the ECAP at the subject's comfort level. Without feedback, the device delivered a fixed current similar to the commercial devices. SCS control with and without feedback were tested in various postures. Subjects compared the strength of the paraesthesia at each posture to the previous posture with 5-point Likert scales.

Subject pain scores, and stimulation side effects were compared between trial stimulation with the commercial device and Saluda feedback stimulation using 5-point Likert scales.

Figure 17A:
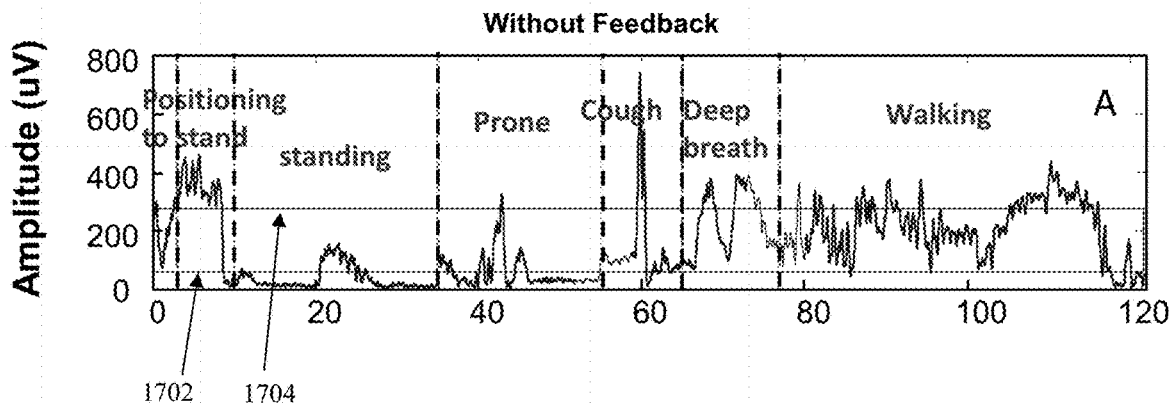
Figure 17B:
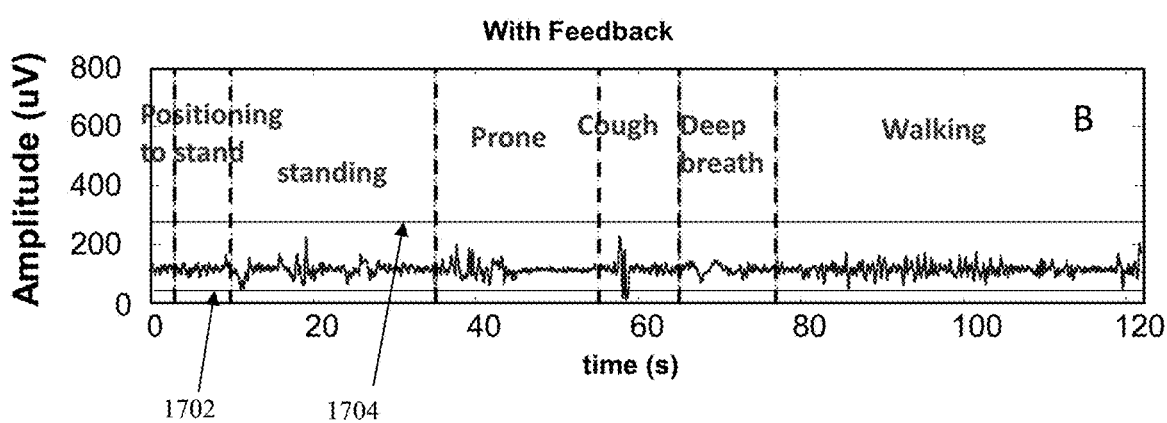
FIG. 17b is a graph showing ECAP amplitude over time during changes in recipient posture, with feedback active.

FIGS. 17a and 17b are graphs showing the observed amplitude of the ECAP in response to the delivery of stimuli over the course of two minutes, during which time the patient changed posture and made movements as indicated. In FIG. 17a, without feedback loop control, it can be seen that a regime of stimuli delivered at a constant amplitude produce ECAPs which vary considerably in amplitude, between zero and 750 uV. In particular, it is noted that this patient received no pain relief when the ECAP amplitude was below therapeutic threshold 1702, so that it can be seen from FIG. 17a that the constant stimulus therapy was mostly failing to deliver pain relief while the patient was standing or lying prone. On the other hand, the comfort threshold 1704 for this patient was also regularly exceeded by the observed ECAP amplitude, in particular at times when the patient was positioning to stand, briefly while prone, during a cough and while taking a deep breath, and repeatedly while walking.

In contrast, in FIG. 17b when ECAPs were recorded with the feedback loop actively controlling the amplitude of the applied stimuli, and while the patient repeated the same sequence of actions, the ECAP amplitudes are kept almost entirely within the therapeutic window, above therapeutic threshold 1702 and below comfort threshold 1704. The occurrence of evoked responses in the overstimulation region above threshold 1704 has been eliminated entirely, while the occurrence of non-therapeutic responses having an amplitude below threshold 1702 has been significantly reduced compared to FIG. 17a.

Figures 18, 19:
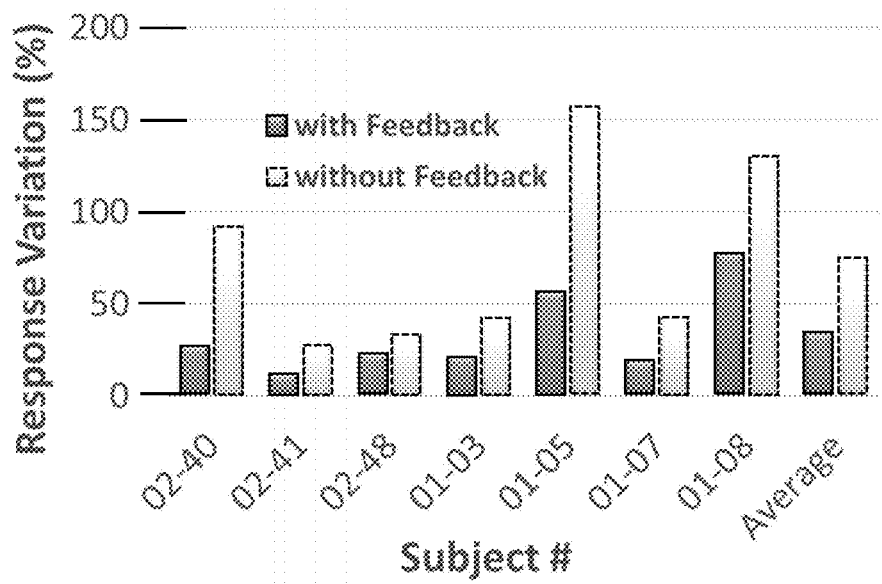
FIG. 18 shows RMS variation of the response from the comfort level.
FIG. 19 shows the comparison of user perception between feedback and non-feedback.

Data of the type shown in FIGS. 17a and 17b, from seven subjects, was processed to determine the variation of the ECAP response from the comfort level, calculated as root mean square (rms) and shown in FIG. 18. The rightmost columns of FIG. 18 show that on average amongst these seven subjects there was 30% variation from the comfort level when feedback was enabled, but more than 70% variation from the comfort level without feedback.

FIG. 19 shows a subjective comparison between feedback and non-feedback. This shows that with feedback, 90% of the subjects have improved pain relief (and no worse side effects) or less side effects (and no worse pain relief).

Figure 20:
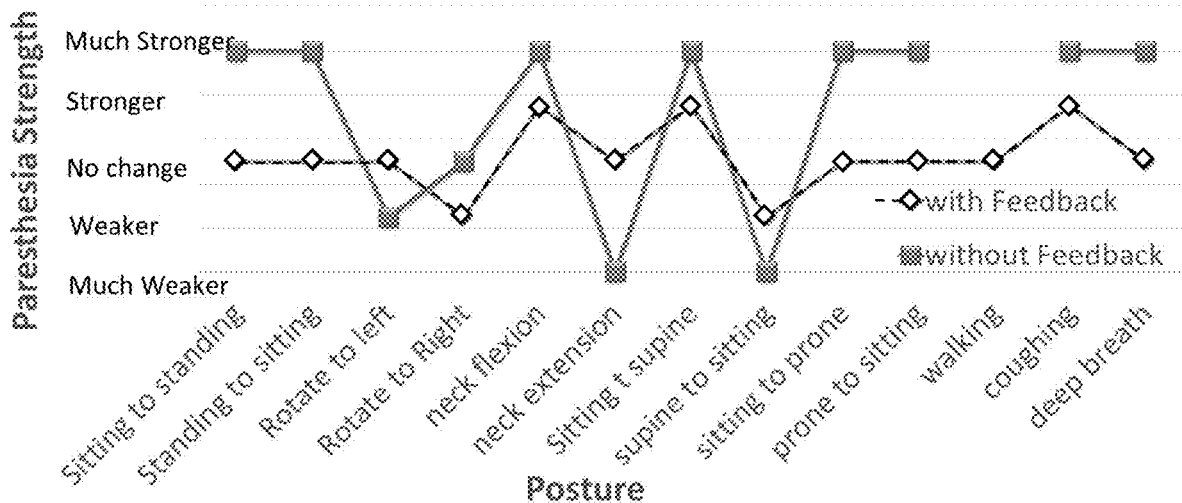
FIG. 20 shows a user's perception of paraesthesia continuity across various postures.

FIG. 20 illustrates subjective data obtained from one patient showing that, as is desirable, the paraesthesia strength has much less variation in every movement or change of posture tested when feedback is enabled, as compared to without feedback.

Figure 21:
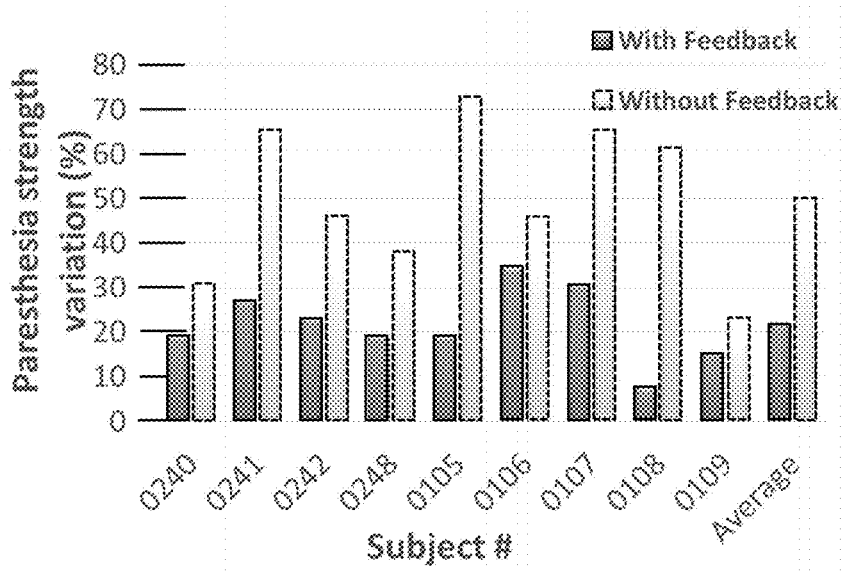
FIG. 21 illustrates perceived paraesthesia variation ratings across postures.

In FIG. 21 the variation in paraesthesia strength across postures was rated from 0% (no change for any posture) to 100% (much stronger or much weaker at each posture). With feedback the perceived variation in paraesthesia strength was significantly (P<0.001) reduced, by 30% as compared to without feedback.

The study of FIGS. 17-21 thus shows that there is a clear correlation between the variation of the response with feedback compared to non-feedback, both when determined directly from measured spinal cord potentials and when determined from the qualitative assessment of the subjects. 87% of the subjects had less side effects with either no difference in pain relief or better pain relief with feedback control, compared with conventional stimulation.

The described electronic functionality can be implemented by discrete components mounted on a printed circuit board, or by a combination of integrated circuits, or by an application-specific integrated circuit (ASIC).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A method of controlling a neural stimulus, the method comprising:
applying the neural stimulus to a neural pathway of a patient in order to give rise to an evoked action potential on the neural pathway, the stimulus being defined by at least one stimulus parameter, wherein the stimulus parameter is stimulus current amplitude;
measuring a neural compound action potential response evoked by the stimulus, and deriving from the measured evoked response a feedback variable, wherein the feedback variable is an amplitude measure of the evoked compound action potential (ECAP);
completing a feedback loop by using the feedback variable to control the at least one stimulus parameter value; and
determining an estimate of a characteristic of a current ECAP growth curve from the stimulus current amplitude and the measured ECAP amplitude.

2. The method of claim 1 wherein the characteristic is a slope P of the current ECAP growth curve.

3. The method of claim 2 wherein an estimate P' of the slope P is determined as $P'=(V+K)/I$, where V is the measured ECAP amplitude, K is a constant or function which relates P to a stimulus threshold T, and I is the stimulus current amplitude.

4. The method of claim 1, wherein the characteristic is a stimulus threshold T of the current ECAP growth curve.

5. The method of claim 1, further comprising adaptively compensating for changes in a gain of the feedback loop caused by electrode movement relative to the neural pathway.

6. The method of claim 5, wherein the adaptively compensating for changes in the gain of the feedback loop comprises maintaining a corner frequency of the feedback loop at a desired value or within a desired range.

7. The method of claim 6, wherein the desired value or range of the corner frequency is selected to suitably attenuate low frequency noise such as heartbeat as well as high frequency noise such as electrical amplifier noise.

8. The method of claim 6, wherein the desired value or range of the corner frequency is selected to bias attenuation of heartbeat and noise while the patient is in a more or most sensitive posture.

9. The method of claim 5, wherein the adaptively compensating comprises introducing the estimate into the feedback loop.

10. The method of claim 9 wherein the characteristic is a slope P of the current ECAP growth curve, and the introducing comprises scaling an error signal of the feedback loop by 1/P' where P' is the estimate of the slope.

11. The method of claim 1 wherein the feedback loop is a first order feedback loop.

12. The method of claim 1 wherein the feedback loop is a second order feedback loop.

13. The method of claim 1 wherein a set point of the feedback loop is configured so as to seek a constant value of ECAP amplitude.

14. The method of claim 1 wherein a set point of the feedback loop is configured so as to seek a target ECAP amplitude which changes over time as defined by a therapy map.

15. A non-transitory computer readable medium for controllably applying a neural stimulus, comprising the following instructions for execution by one or more processors:
  computer program code means for applying the neural stimulus to a neural pathway of a patient in order to give rise to an evoked action potential on the neural pathway, the stimulus being applied as defined by at least one stimulus parameter, wherein the stimulus parameter is stimulus current amplitude;
  computer program code means for measuring a neural compound action potential response evoked by the stimulus and deriving from the measured evoked response a feedback variable, wherein the feedback variable is an amplitude measure of the evoked compound action potential (ECAP);
  computer program code means for completing a feedback loop by using the feedback variable to control the at least one stimulus parameter value; and
computer program code means for determining an estimate of a characteristic of a current ECAP growth curve from the stimulus current amplitude and the measured ECAP amplitude.

16. An implantable device for controllably applying a neural stimulus, the device comprising:
  a plurality of electrodes including one or more nominal stimulus electrodes and one or more nominal sense electrodes;
  a stimulus source for providing a stimulus to be delivered from the one or more stimulus electrodes to a neural pathway of a patient in order to give rise to an evoked action potential on the neural pathway;
  measurement circuitry for recording a neural compound action potential signal sensed at the one or more sense electrodes; and
  a control unit configured to:
    control application of a neural stimulus as defined by at least one stimulus parameter, wherein the stimulus parameter is stimulus current amplitude;
    measure via the measurement circuitry a neural compound action potential response evoked by the stimulus;
    determine from the measured evoked response a feedback variable, wherein the feedback variable is an amplitude measure of the evoked compound action potential (ECAP);
    complete a feedback loop by using the feedback variable to control the at least one stimulus parameter value; and
    determining an estimate of a characteristic of a current ECAP growth curve from the stimulus current amplitude and the measured ECAP amplitude.

17. The implantable device of claim 16, wherein the characteristic is a slope P of the current ECAP growth curve.

18. The implantable device of claim 17 wherein the control unit is configured to determine an estimate P' of the slope P as $P'=(V+K)/I$, where V is the measured ECAP amplitude, K is a constant or function which relates P to a stimulus threshold T, and I is the stimulus current amplitude.

19. The implantable device of claim 16, wherein the characteristic is a stimulus threshold T of the current ECAP growth curve.

20. The implantable device of claim 16 wherein the control unit is further configured to adaptively compensate for changes in a gain of the feedback loop caused by electrode movement relative to the neural pathway.

21. The implantable device of claim 20 wherein the control unit is configured to adaptively compensate for changes in the gain of the feedback loop by maintaining a corner frequency of the feedback loop at a desired value or within a desired range.

22. The implantable device of claim 21 wherein the desired value or range of the corner frequency is selected to suitably attenuate low frequency noise such as heartbeat as well as high frequency noise such as electrical amplifier noise.

23. The implantable device of claim 21, wherein the desired value or range of the corner frequency is selected to bias attenuation of heartbeat and noise while the patient is in a more or most sensitive posture.

24. The implantable device of claim 23, wherein the control unit is configured to adaptively compensate for changes in the gain of the feedback loop by introducing the estimate into the feedback loop.

25. The implantable device of claim 20 wherein the characteristic is a slope P of the current ECAP growth curve, and the control unit is configured to scale an error signal of the feedback loop by 1/P' where P' is the estimate of the slope.

26. The implantable device of claim 16, wherein the feedback loop is a first order feedback loop.

27. The implantable device of claim 16, wherein the feedback loop is a second order feedback loop.

28. The implantable device of claim 16, wherein a set point of the feedback loop is configured so as to seek a constant value of ECAP amplitude.

29. The implantable device of claim 16, wherein a set point of the feedback loop is configured so as to seek a target ECAP amplitude which changes over time as defined by a therapy map.

\* \* \* \* \*